(12) United States Patent
Lundquist et al.

(10) Patent No.: US 10,487,356 B2
(45) Date of Patent: Nov. 26, 2019

(54) INTEGRATED DEVICES AND SYSTEMS FOR FREE-SPACE OPTICAL COUPLING

(71) Applicant: Pacific Biosciences of California, Inc., Menlo Park, CA (US)

(72) Inventors: Paul Lundquist, San Francisco, CA (US); Mark McDonald, Milpitas, CA (US); Aaron Rulison, Los Altos, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 515 days.

(21) Appl. No.: 15/072,146

(22) Filed: Mar. 16, 2016

(65) Prior Publication Data

US 2016/0273034 A1   Sep. 22, 2016

Related U.S. Application Data

(60) Provisional application No. 62/133,965, filed on Mar. 16, 2015, provisional application No. 62/175,139, filed on Jun. 12, 2015.

(51) Int. Cl.
*C12Q 1/6874* (2018.01)
*G01N 21/64* (2006.01)
(Continued)

(52) U.S. Cl.
CPC ......... *C12Q 1/6874* (2013.01); *G01N 21/648* (2013.01); *G01N 21/6452* (2013.01);
(Continued)

(58) Field of Classification Search
None
See application file for complete search history.

(56) References Cited

U.S. PATENT DOCUMENTS

| 4,634,215 A | 1/1987 | Reule |
| 4,645,523 A | 2/1987 | Howard et al. |

(Continued)

FOREIGN PATENT DOCUMENTS

| EP | 1105529 B1 | 11/2005 |
| EP | 1871902 B1 | 10/2006 |

(Continued)

OTHER PUBLICATIONS

Abbas et al. (2011) Sens. Actuators B Chem. 156:169-175.
(Continued)

*Primary Examiner* — Jill A Warden
*Assistant Examiner* — Brittany I Fisher
(74) *Attorney, Agent, or Firm* — VLP Law Group LLP

(57) ABSTRACT

Optical delivery devices and integrated analytical systems comprising the optical delivery devices are provided. The optical delivery devices include optical inputs, optical outputs, and integrated optical waveguides that are configured for coupling of optical energy to a target waveguide device through free space. The integrated analytical systems include the optical delivery devices in combination with the target waveguide device. The devices and systems are useful in the analysis of highly multiplexed optical reactions in large numbers at high densities, including biochemical reactions, such as nucleic acid sequencing reactions. The devices provide for the efficient coupling of optical excitation energy from an optical source to the optical reactions. Optical signals emitted from the reactions can thus be measured with high sensitivity and discrimination. The devices and systems are well suited for miniaturization and high throughput.

32 Claims, 20 Drawing Sheets

(51) Int. Cl.
*G02B 6/30* (2006.01)
*G02B 6/125* (2006.01)
*G02B 6/34* (2006.01)
*G01N 21/77* (2006.01)

(52) U.S. Cl.
CPC ............ *G01N 21/7703* (2013.01); *G01N 2201/06113* (2013.01); *G01N 2201/08* (2013.01); *G02B 6/125* (2013.01); *G02B 6/30* (2013.01); *G02B 6/34* (2013.01)

(56) References Cited

U.S. PATENT DOCUMENTS

| | | |
|---|---|---|
| 5,033,812 A | 7/1991 | Yoshida et al. |
| 5,082,629 A | 1/1992 | Burgess, Jr. et al. |
| 5,094,517 A | 3/1992 | Franke |
| 5,101,459 A | 3/1992 | Sunagawa |
| 5,135,876 A | 8/1992 | Andrade et al. |
| 5,157,262 A | 10/1992 | Marsoner et al. |
| 5,159,661 A | 10/1992 | Ovshinsky et al. |
| 5,173,747 A | 12/1992 | Boiarski et al. |
| 5,192,502 A | 3/1993 | Attridge et al. |
| 5,233,673 A | 8/1993 | Vali et al. |
| 5,239,178 A | 8/1993 | Derndinger et al. |
| 5,439,647 A | 8/1995 | Saini |
| 5,446,534 A | 8/1995 | Goldman |
| 5,470,710 A | 11/1995 | Weiss et al. |
| 5,502,467 A | 3/1996 | Li et al. |
| 5,545,531 A | 8/1996 | Rava et al. |
| 5,578,832 A | 11/1996 | Trulson et al. |
| 5,605,662 A | 2/1997 | Heller et al. |
| 5,631,734 A | 5/1997 | Stern et al. |
| 5,677,196 A | 10/1997 | Herron et al. |
| 5,695,934 A | 12/1997 | Brenner |
| 5,744,305 A | 4/1998 | Fodor et al. |
| 5,812,709 A | 9/1998 | Arai et al. |
| 5,821,058 A | 10/1998 | Smith et al. |
| 5,832,165 A | 11/1998 | Reichert et al. |
| 5,867,266 A | 2/1999 | Craighead et al. |
| 5,919,712 A | 7/1999 | Herron et al. |
| 6,002,520 A | 12/1999 | Hoch et al. |
| 6,071,748 A | 6/2000 | Modlin et al. |
| 6,192,168 B1 | 2/2001 | Feldstein et al. |
| 6,210,896 B1 | 4/2001 | Chan |
| 6,236,945 B1 | 5/2001 | Simpson et al. |
| 6,239,891 B1 | 5/2001 | Nakama |
| 6,263,286 B1 | 7/2001 | Gilmanshin et al. |
| 6,325,977 B1 | 12/2001 | Theil |
| 6,388,788 B1 | 5/2002 | Harris et al. |
| 6,437,345 B1 | 8/2002 | Bruno-Raumandi et al. |
| 6,438,279 B1 | 8/2002 | Craighead et al. |
| 6,603,537 B1 | 8/2003 | Dietz et al. |
| 6,611,634 B2 | 8/2003 | Herron et al. |
| 6,690,002 B2 | 2/2004 | Kuroda et al. |
| 6,699,655 B2 | 3/2004 | Nikiforov et al. |
| 6,760,499 B2 | 7/2004 | Pezeshki et al. |
| 6,778,739 B1 * | 8/2004 | Jerphagnon ........ G02B 6/12011 385/17 |
| 6,784,982 B1 | 8/2004 | Blumenfeld et al. |
| 6,800,860 B2 | 10/2004 | Dietz et al. |
| 6,818,395 B1 | 11/2004 | Quake et al. |
| 6,856,751 B2 | 2/2005 | Oaknin et al. |
| 6,867,851 B2 | 3/2005 | Blumenfeld et al. |
| 6,917,726 B2 | 7/2005 | Levene et al. |
| 6,919,211 B1 | 7/2005 | Fodor et al. |
| 6,973,232 B2 | 12/2005 | Betty et al. |
| 6,979,830 B2 | 12/2005 | Dietz et al. |
| 6,982,146 B1 | 1/2006 | Schneider et al. |
| 6,987,613 B2 | 1/2006 | Pocius et al. |
| 7,013,054 B2 | 3/2006 | Levene et al. |
| 7,022,515 B2 | 4/2006 | Herron et al. |
| 7,056,661 B2 | 6/2006 | Korlach et al. |
| 7,057,832 B2 | 6/2006 | Wu et al. |
| 7,075,695 B2 | 7/2006 | Gronbach |
| 7,081,954 B2 | 7/2006 | Sandstrom |
| 7,083,914 B2 | 8/2006 | Seul et al. |
| 7,130,041 B2 | 10/2006 | Bouzid et al. |
| 7,135,667 B2 | 11/2006 | Oldham et al. |
| 7,139,074 B2 | 11/2006 | Reel |
| 7,145,645 B2 | 12/2006 | Blumenfeld et al. |
| 7,146,087 B2 | 12/2006 | Heideman et al. |
| 7,150,997 B2 | 12/2006 | Kovacs |
| 7,170,050 B2 | 1/2007 | Turner et al. |
| 7,175,811 B2 | 2/2007 | Bach et al. |
| 7,181,122 B1 | 2/2007 | Levene et al. |
| 7,189,361 B2 | 3/2007 | Carson |
| 7,197,196 B2 | 3/2007 | Lin et al. |
| 7,199,357 B1 | 4/2007 | Oldham et al. |
| 7,209,836 B1 | 4/2007 | Schermer et al. |
| 7,227,128 B2 | 6/2007 | Sagatelyan |
| RE39,772 E | 8/2007 | Herron et al. |
| 7,257,141 B2 | 8/2007 | Chua |
| 7,302,348 B2 | 11/2007 | Ghosh et al. |
| 7,315,019 B2 | 1/2008 | Turner et al. |
| 7,323,681 B1 | 1/2008 | Oldham et al. |
| 7,400,380 B2 | 7/2008 | Hahn |
| 7,486,865 B2 | 2/2009 | Foquet et al. |
| 7,499,094 B2 | 3/2009 | Kuriyama |
| 7,537,734 B2 | 5/2009 | Reichert et al. |
| 7,583,875 B2 | 9/2009 | Yamauchi et al. |
| 7,709,808 B2 | 5/2010 | Reel et al. |
| 7,767,441 B2 | 8/2010 | Chiou et al. |
| 7,811,810 B2 | 10/2010 | Chiou et al. |
| 7,817,281 B2 | 10/2010 | Kiesel et al. |
| 7,820,983 B2 | 10/2010 | Lundquist et al. |
| 7,834,329 B2 | 11/2010 | Lundquist et al. |
| 7,838,847 B2 | 11/2010 | Lundquist et al. |
| 7,907,800 B2 | 3/2011 | Foquet et al. |
| 8,053,742 B2 | 11/2011 | Lundquist et al. |
| 8,207,509 B2 | 6/2012 | Lundquist et al. |
| 8,247,216 B2 | 8/2012 | Zaccarin et al. |
| 8,264,936 B2 | 9/2012 | Tanaka et al. |
| 8,274,040 B2 | 9/2012 | Zhong et al. |
| 8,411,375 B2 | 4/2013 | Lenchenkov |
| 8,465,699 B2 | 6/2013 | Fehr et al. |
| 8,467,061 B2 | 6/2013 | McCaffrey et al. |
| 8,471,219 B2 | 6/2013 | Lundquist et al. |
| 8,618,507 B1 | 12/2013 | Lundquist et al. |
| 8,906,320 B1 | 12/2014 | Eltoukhy et al. |
| 9,029,802 B2 | 5/2015 | Lundquist et al. |
| 9,223,084 B2 | 12/2015 | Grot et al. |
| 9,372,308 B1 | 6/2016 | Saxena et al. |
| 2002/0034457 A1 | 3/2002 | Reichert et al. |
| 2002/0110839 A1 * | 8/2002 | Bach ................. B82Y 5/00 435/7.9 |
| 2002/0113213 A1 | 8/2002 | Amirkhanian et al. |
| 2002/0146047 A1 | 10/2002 | Bendett et al. |
| 2002/0154376 A1 | 10/2002 | Vail et al. |
| 2002/0197010 A1 | 12/2002 | Kato et al. |
| 2003/0044781 A1 | 3/2003 | Korlach et al. |
| 2003/0132406 A1 | 7/2003 | Waldhausl et al. |
| 2003/0138180 A1 | 7/2003 | Kondo |
| 2003/0174324 A1 | 9/2003 | Sandstrom |
| 2003/0174992 A1 | 9/2003 | Levene et al. |
| 2004/0040868 A1 | 3/2004 | Denuzzio et al. |
| 2004/0046128 A1 | 3/2004 | Abel et al. |
| 2004/0197793 A1 | 10/2004 | Hassibi et al. |
| 2004/0249227 A1 | 12/2004 | Klapproth et al. |
| 2005/0006607 A1 | 1/2005 | Winter et al. |
| 2005/0014178 A1 | 1/2005 | Holm-Kennedy |
| 2005/0135974 A1 | 6/2005 | Harvey et al. |
| 2005/0175273 A1 | 8/2005 | Iida et al. |
| 2005/0185915 A1 * | 8/2005 | Yu ................. G02B 6/0016 385/146 |
| 2005/0201899 A1 | 9/2005 | Weisbuch |
| 2005/0206895 A1 | 9/2005 | Salmelainen |
| 2006/0060766 A1 | 3/2006 | Turner et al. |
| 2006/0068412 A1 * | 3/2006 | Tang ................. B82Y 15/00 435/6.11 |
| 2006/0103850 A1 | 5/2006 | Alphonse et al. |
| 2007/0036511 A1 | 2/2007 | Lundquist et al. |
| 2007/0081782 A1 | 4/2007 | Maeda et al. |
| 2007/0099212 A1 | 5/2007 | Harris |
| 2007/0134128 A1 | 6/2007 | Korlach |

(56) References Cited

U.S. PATENT DOCUMENTS

| | | |
|---|---|---|
| 2007/0146701 A1 | 6/2007 | Kiesel et al. |
| 2007/0188746 A1 | 8/2007 | Kraus et al. |
| 2007/0196815 A1 | 8/2007 | Lappe et al. |
| 2008/0002929 A1 | 1/2008 | Bowers et al. |
| 2008/0020938 A1 | 1/2008 | Kaplan |
| 2008/0039339 A1 | 2/2008 | Hassibi et al. |
| 2008/0056950 A1 | 3/2008 | Weisbuch et al. |
| 2008/0099430 A1 | 5/2008 | Brooks et al. |
| 2008/0128627 A1 | 6/2008 | Lundquist et al. |
| 2008/0161195 A1 | 7/2008 | Turner et al. |
| 2008/0176769 A1 | 7/2008 | Rank et al. |
| 2008/0212960 A1 | 9/2008 | Lundquist et al. |
| 2008/0304802 A1 | 12/2008 | Watanabe et al. |
| 2009/0060526 A1 | 3/2009 | Matsui et al. |
| 2009/0142790 A1* | 6/2009 | Fang ............... G01N 33/54373 |
| | | 435/29 |
| 2009/0146076 A1 | 6/2009 | Chiou et al. |
| 2009/0168151 A1 | 7/2009 | Ruschin et al. |
| 2009/0181396 A1 | 7/2009 | Luong et al. |
| 2009/0208957 A1 | 8/2009 | Korlach et al. |
| 2009/0245718 A1* | 10/2009 | Li ............... B82Y 20/00 |
| | | 385/12 |
| 2009/0247414 A1 | 10/2009 | Obradovic |
| 2009/0286245 A1* | 11/2009 | Bjornson ............ C12Q 1/6869 |
| | | 435/6.18 |
| 2009/0311774 A1 | 12/2009 | Chiou et al. |
| 2009/0312188 A1 | 12/2009 | Duer et al. |
| 2010/0065726 A1 | 3/2010 | Zhong et al. |
| 2010/0099100 A1 | 4/2010 | Zaccarin et al. |
| 2010/0121582 A1 | 5/2010 | Pan et al. |
| 2010/0163521 A1 | 7/2010 | Balamane et al. |
| 2010/0220261 A1* | 9/2010 | Mizushima ............ G02B 6/0035 |
| | | 349/64 |
| 2010/0255488 A1 | 10/2010 | Kong et al. |
| 2010/0256918 A1 | 10/2010 | Chen et al. |
| 2010/0295083 A1 | 11/2010 | Celler |
| 2011/0117637 A1 | 5/2011 | Gray et al. |
| 2011/0183409 A1 | 7/2011 | Newby et al. |
| 2011/0210094 A1 | 9/2011 | Gray et al. |
| 2011/0222179 A1 | 9/2011 | Monadgemi |
| 2011/0223590 A1 | 9/2011 | Chiou et al. |
| 2011/0255303 A1* | 10/2011 | Nichol ............... G02B 6/006 |
| | | 362/606 |
| 2011/0257040 A1 | 10/2011 | Turner et al. |
| 2011/0306039 A1 | 12/2011 | Chiou et al. |
| 2012/0002395 A1 | 1/2012 | Du et al. |
| 2012/0014837 A1 | 1/2012 | Fehr et al. |
| 2012/0019828 A1 | 1/2012 | McCaffrey et al. |
| 2012/0021525 A1 | 1/2012 | Fehr et al. |
| 2012/0052506 A1 | 3/2012 | Yue et al. |
| 2012/0058469 A1 | 3/2012 | Shen et al. |
| 2012/0058473 A1 | 3/2012 | Yue et al. |
| 2012/0058482 A1 | 3/2012 | Shen et al. |
| 2012/0077189 A1 | 3/2012 | Shen et al. |
| 2012/0085894 A1 | 4/2012 | Zhong et al. |
| 2012/0092750 A1* | 4/2012 | Kroll ............... G02B 6/0046 |
| | | 359/291 |
| 2012/0156100 A1 | 6/2012 | Tsai et al. |
| 2012/0224149 A1* | 9/2012 | Tominaga ............ G02B 5/3033 |
| | | 353/20 |
| 2013/0043552 A1 | 2/2013 | Lazarov et al. |
| 2013/0071850 A1* | 3/2013 | Duer ............... G01N 21/553 |
| | | 435/6.12 |
| 2013/0148682 A1 | 6/2013 | Zhang et al. |
| 2014/0029894 A1* | 1/2014 | Bowen ............... G02B 6/30 |
| | | 385/37 |
| 2014/0094375 A1* | 4/2014 | Kamtekar ...... C12Y 207/07007 |
| | | 506/2 |
| 2014/0177995 A1 | 6/2014 | Mohammed et al. |
| 2014/0193331 A1 | 7/2014 | Naczynski et al. |
| 2014/0199016 A1* | 7/2014 | Grot ............... G02B 6/10 |
| | | 385/11 |
| 2014/0240951 A1 | 8/2014 | Brady et al. |
| 2014/0241682 A1 | 8/2014 | Sandhu et al. |
| 2014/0287964 A1 | 9/2014 | Lundquist et al. |
| 2014/0353577 A1 | 12/2014 | Agarwal et al. |
| 2015/0001175 A1 | 1/2015 | Rabiei |
| 2015/0141267 A1 | 5/2015 | Rothberg et al. |
| 2015/0286060 A1 | 10/2015 | Roh et al. |
| 2016/0061740 A1 | 3/2016 | Grot et al. |
| 2016/0154165 A1 | 6/2016 | Grot et al. |
| 2016/0216538 A1 | 7/2016 | McDonald et al. |

FOREIGN PATENT DOCUMENTS

| | | |
|---|---|---|
| EP | 2362209 A2 | 8/2011 |
| KR | 10-2005-0088782 A | 9/2005 |
| WO | WO 1991006678 A1 | 5/1991 |
| WO | WO 2000052518 A1 | 9/2000 |
| WO | WO 2001016375 A2 | 3/2001 |
| WO | WO 2004100068 A2 | 11/2004 |
| WO | WO 2006116726 A2 | 2/2006 |
| WO | 2006061783 A1 | 6/2006 |
| WO | WO 2006135782 A2 | 12/2006 |
| WO | WO 2007002367 A2 | 1/2007 |
| WO | WO 2007011549 A1 | 1/2007 |
| WO | WO 2008002765 A2 | 1/2008 |
| WO | WO 2009056065 A1 | 5/2009 |
| WO | WO 2009131535 A1 | 10/2009 |
| WO | WO 2009149125 A2 | 12/2009 |
| WO | WO 2010051773 A1 | 5/2010 |
| WO | WO 2010102567 A1 | 9/2010 |
| WO | WO 2011076132 A2 | 6/2011 |
| WO | WO 2012064472 A2 | 5/2012 |
| WO | 2012129068 A1 | 9/2012 |
| WO | WO 2014031157 A1 | 2/2014 |
| WO | WO 2014064228 A1 | 5/2014 |

OTHER PUBLICATIONS

Balakrishnan "Planar Lightwave Circuits Enable Next-Generation 40G/100G Networks".
Barrios (2006) IEEE Photon Technol. Lett. 18:2419.
Barrios et al. (2007) Optics Letters 32:3080.
Barrios et al. (2008) Optics Letters 33:708.
Bernini et al. (2005) Proc. SPIE 5728:101-111.
Boiarski et al. (1992) Proc. SPIE 1793:199-211.
Budach et al. (1999) Anal. Chem. 71(16):3347-3355.
Chen et al. (2012) Optics Letters 37:2814.
Cottier et al. (2002) Proc. SPIE 4616:53-63.
Deopura, M. et al. (2001) Optics Lett 26(15):1197-1199.
Duveneck et al. (2002) Anal Chem Acta 469:49-61.
Eid et al. (2009) Science 323:133.
Feldstein et al. (1999) J. Biomed Microdev. 1:139-153.
Feng et al. (2006) IEEE J. Quantum Electron. 42:885.
Feng et al. (2007) Optics Letters 32:2131.
Fink, Y. et al. (1998) Science 282:1679-1682.
Fonollosa et al. (2006) Proceedings of SPIE 61860R-1: 61860R-11.
Herron et al. (2003) Biopolymers at Interfaces 2nd Ed, Surfactant Science Series vol. 110, Marcel Dekker, NY pp. 115-163.
Laurell et al. (2012) Optics Express 20:22308.
Levene, M.J. et al. (2003) Science 299:682-686.
Lim et al. (2006) IEEE Journal of Selected Topics in Quantum Electronics 12(6):1461-1468.
Mortazavi et al. (1994) Optics Letters 19:1290.
Nava et al. (2010) Electronics Letters 46:1686.
Pan et al. (2011) Optics Communications 284:429.
Psaltis et al. (2006) Nature 442:381.
Robinson et al. (2008) Optics Express 16:4296.
Sahin et al. (2011) J. Nanophoton. 5:051812.
Salama et al. (2004) Biosensors & Bioelectronics 19:1377-1386.
Song et al. (2012) Optics Express 20:22290.
Sun et al. (2007) Optics Express 15:17967.
Weissman et al. (1999) Proc. SPIE 3596:210-216.
Wu et al. (2006) Biosensors and Bioelectronics 21:1252-1263.
Yao et al. (2012) Nonlinear Optics and Solid-State Lasers, Springer-Verlag Berlin Heidelberg, Chapter 5.
Yariv, A. et al. (1977) IEEE J Quantum Elec QE-13(4):233-253.

(56) References Cited

OTHER PUBLICATIONS

International Search Report and Written Opinion dated Jun. 16, 2016 for related PCT/US2016/022684.
Jul. 19, 2018 Extended European Search Report in counterpart EP 16 765 677.6.

* cited by examiner

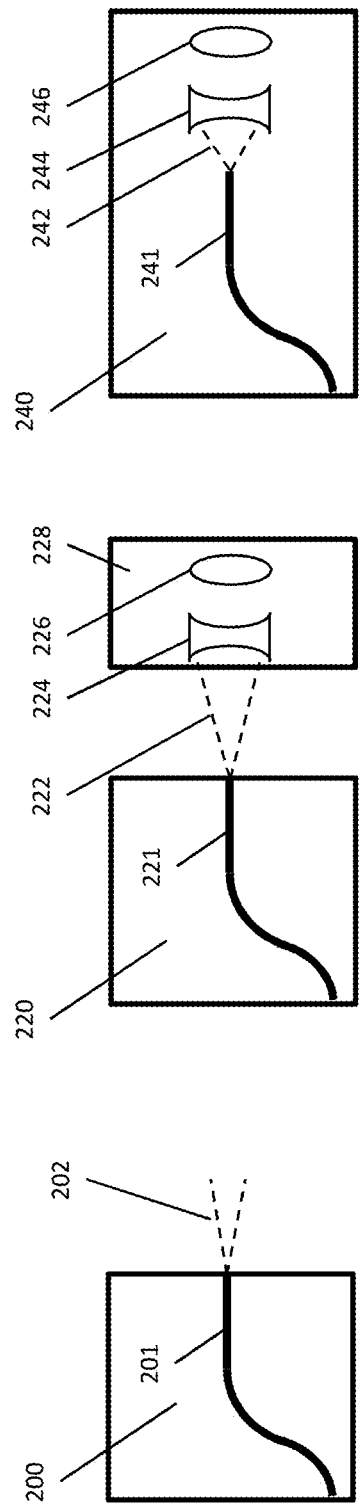

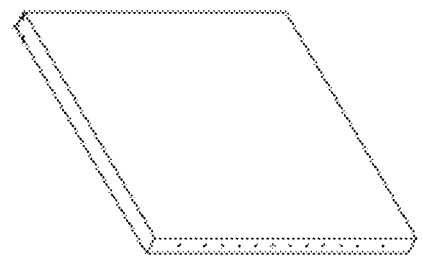
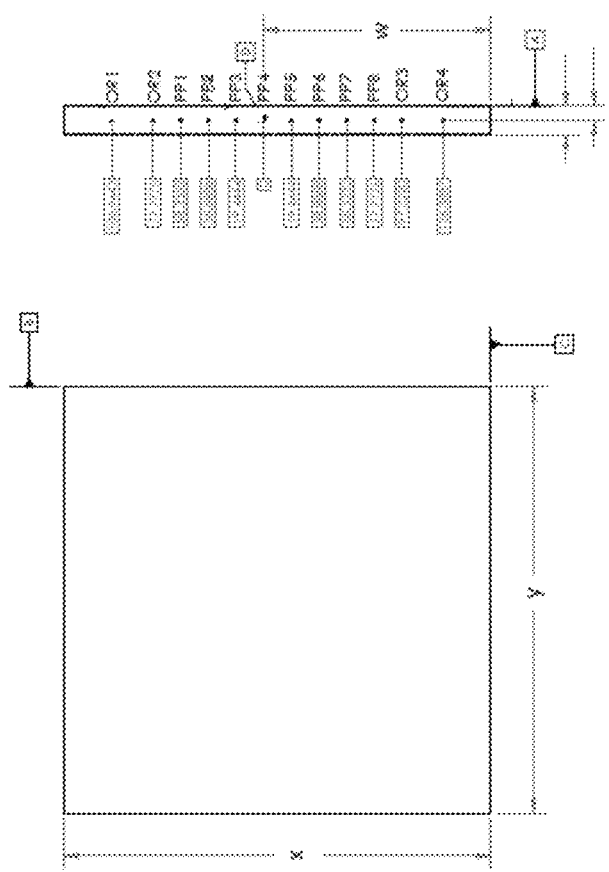
FIG. 12B
FIG. 12A

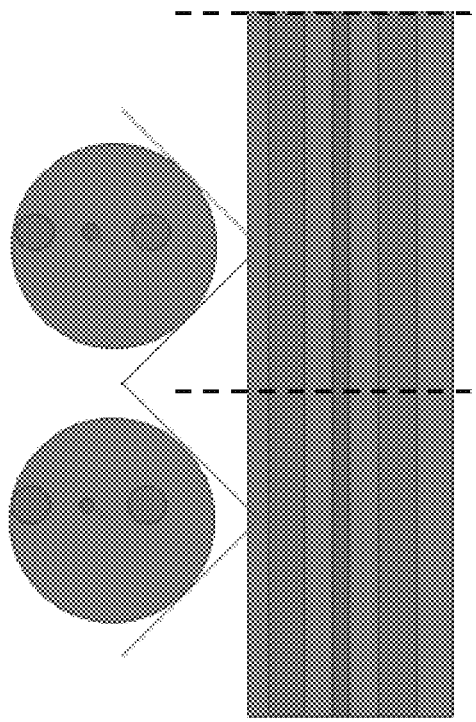
FIG. 16A
FIG. 16B
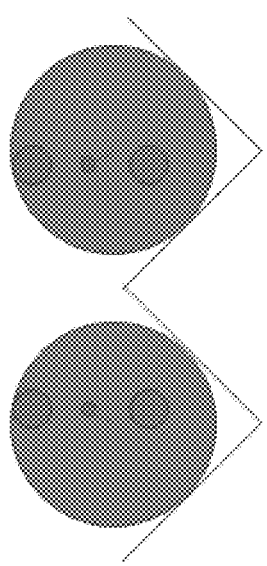
FIG. 15

INTEGRATED DEVICES AND SYSTEMS FOR FREE-SPACE OPTICAL COUPLING

CROSS-REFERENCE TO RELATED APPLICATIONS

This application claims the benefit of U.S. Provisional Application No. 62/133,965, filed on Mar. 16, 2015, and 62/175,139, filed on Jun. 12, 2015, the disclosures of which are each incorporated herein by reference in their entireties.

BACKGROUND OF THE INVENTION

As multiplexed optical analytical systems continue to be miniaturized in size, expanded in scale, and increased in power, the need to develop improved systems capable of delivering optical energy to such systems becomes more important. For example, highly multiplexed analytical systems comprising integrated waveguides for the illumination of nanoscale samples are described in U.S. Patent Application Publication Nos. 2008/0128627 and 2012/0085894. Further optical systems for the analysis of nanoscale samples, including the illumination and detection of such samples, are described in U.S. Patent Application Publication Nos. 2012/0014837, 2012/0021525, and 2012/0019828. Additional nanoscale illumination systems for highly multiplexed analysis are described in U.S. Patent Application Publication Nos. 2014/0199016 and 2014/0287964.

In conventional optical systems, optical trains are typically employed to direct, focus, filter, split, separate, and detect light to and from the sample materials. Such systems typically employ an assortment of different optical elements to direct, modify, and otherwise manipulate light entering and leaving a reaction site. Such systems are frequently complex and costly and tend to have significant space requirements. For example, typical systems employ mirrors and prisms in directing light from its source to a desired destination. Additionally, such systems can include light-splitting optics such as beam-splitting prisms to generate two or more beams from a single original beam.

Alternatives to the conventional optical systems have been described, in particular alternative systems having integrated optical components designed and fabricated within highly confined environments. For example, planar lightwave circuits (PLCs) comprising fiber interfaces, wavelength filters or combiners, phase-delayed optical interferometers, optical isolators, polarization control, and/or taps have been developed for use in telecommunications applications. In some cases these devices additionally include one or more laser sources and one or more optical detectors. The devices use integrated optical waveguides to route photons through an optical circuit, in much the same way as electrons are routed through an electrical circuit. They are fabricated using standard semiconductor fabrication techniques, and they can accordingly integrate both passive components, such as optical filters and fiber pigtail connectors, and active elements, such as optical switches and attenuators, during the fabrication process. As used in telecommunications equipment, they typically serve to couple and/or split optical signals from fiber optic cores, for the purpose of, for example, multiplexing/demultiplexing, optical branching, and/or optical switching. The devices thus provide the functionality of a more traditional optical train, while at the same time being significantly less expensive, more compact, and more robust.

The PLCs used in telecommunications applications are typically mechanically aligned and bonded to their laser light source and to their associated photodetectors during the manufacturing process. They are therefore not well suited for use in connection with an analytical system having a removable sample holder, where the optical output from an optical delivery device, such as a traditional optical train, is normally coupled to the target sample holder through free space. The optical signal from the output delivery device therefore needs to be aligned with the target device each time the target device is replaced, and the alignment can even need to be monitored and maintained during the course of an analysis, due to mechanical, thermal, and other interfering factors associated with the integrated system during the analysis. In addition, the PLCs used in telecommunications applications are not designed to carry the intensity of optical energy necessary to analyze the large numbers of nanoscale samples present in the highly-multiplexed analytical systems described above, nor are they designed for use with optical sources having wavelengths suitable for use in analytical systems with standard biological reagents.

There is thus a need to improve the performance and properties of optical delivery devices and systems for their use in these applications.

SUMMARY OF THE INVENTION

The present disclosure addresses these and other needs by providing in one aspect an optical delivery device comprising:

an optical input;
an optical output;
an optical output waveguide disposed on a substrate and optically connected to the optical input and the optical output;
wherein the optical output is configured for optical coupling to a target waveguide device through free space.

In some embodiments, the numerical aperture of the optical output of the delivery device is modulated.

In some embodiments, the device is configured to illuminate a footprint on the target waveguide device.

In some embodiments, the optical output waveguide of the device comprises a power modulator.

In some embodiments, the device comprises one or more splitting elements.

In some embodiments, the device comprises one or more phase modulators, amplitude modulators, frequency modulators, mode strippers, or a combination thereof.

In some embodiments, the device is configured for optical output of visible light to a target waveguide device.

In another aspect, the disclosure provides an analytical system comprising:

an integrated optical delivery device; and
an integrated target waveguide device.

In specific system embodiments, the integrated optical delivery device is a delivery device as disclosed herein.

In other specific system embodiments, the system further comprises an alignment device that can provide for dynamic alignment of the integrated target waveguide device and the integrated optical delivery device. In some specific embodiments, the target waveguide device comprises an alignment feature. In some specific embodiments, the target waveguide device comprises a grating coupler.

In preferred system embodiments, the integrated target waveguide device is a multiplexed DNA sequencing device.

In some embodiments, the system comprises an intervening optical element, such as an optical lens element, between the integrated optical delivery device and the integrated target waveguide device. In some of these embodiments, the integrated optical delivery device comprises a plurality of optical outputs, wherein at least one of the plurality of optical outputs has a numerical aperture of no more than 0.1. In specific embodiments, the integrated target waveguide device comprises a grating coupler optically coupled to an integrated waveguide, wherein the grating coupler has a numerical aperture lower than the numerical aperture of the optical output of the optical delivery device. Even more specifically, the grating coupler has a numerical aperture of no more than 0.05.

BRIEF DESCRIPTION OF THE DRAWINGS

FIGS. 2A-2C illustrate schematically three optical device designs, where the optical outputs are configured for coupling through free space.

FIG. 6A: An output grating delivers light from a 2% tap to a detector located above the chip; FIG. 6B: A PIN diode is mounted on the side of the chip to receive light from a 2% tap; FIGS. 6C and 6D: A camera is used to monitor light through free space either on top of the chip or to the side of the chip; FIG. 6E: An exemplary configuration showing that the power-monitoring taps can cross one another. Here, power outputs from four waveguides can be monitored in series from the side of the chip.

FIG. 8A: An optical delivery device coupling two optical inputs, each of which passes through a 1×4 equal power splitter to generate 8 equal-power optical outputs. FIG. 8B: An optical delivery device coupling 8 optical inputs to generate 8 equal-power optical outputs. FIG. 8C: An optical delivery device coupling 4 optical inputs, each of which passes through a 1×2 splitter to generate 8 equal-power optical outputs.

FIG. 12A shows a side view and an end view of an exemplary integrated device, where the end view shows the optical outputs. Distances from the optical output labeled "PP4" are shown in microns. FIG. 12B is a perspective drawing of the same device.

FIG. 15 shows a 2-fiber V-groove fiber array with fibers having poor concentricity and a flipped orientation within the array.

FIG. 16A and FIG. 16B illustrate the use of sequential segments of cut fiber in a 2-fiber V-groove fiber array.

DETAILED DESCRIPTION OF THE INVENTION

Integrated Optical Delivery Devices

Figure 1B:
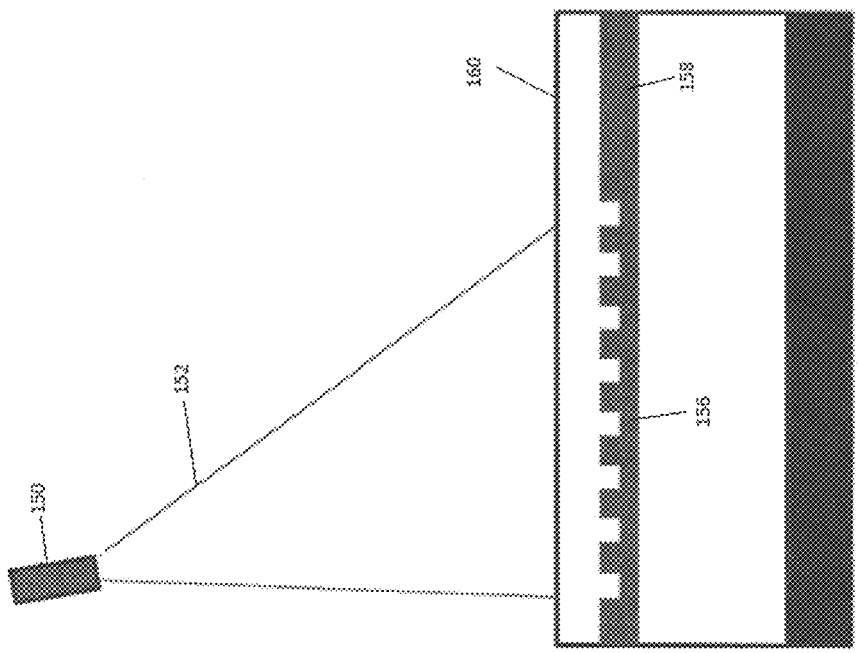
FIGS. 1A-1C illustrate differences between coupling from a fiber tip and coupling through free space to a target waveguide device.

In one aspect, the instant disclosure provides devices for delivering optical energy from one or more external sources, e.g., one or more lasers, to the optical inputs of an associated target integrated waveguide device, such as the optical inputs of a multiplexed integrated DNA sequencing chip. Such optical inputs on the target device are preferably diffractive grating inputs, although other optical inputs can be usefully coupled to the outputs of the instant optical delivery devices. Furthermore, the target integrated waveguide devices preferably have multiple optical inputs, so that the optical energy is transmitted through independent waveguide pathways within the target device. Accordingly, the instant integrated optical delivery devices, also known as "light brush" devices, comprise at least one optical input, at least one optical output, and at least one optical waveguide disposed on a substrate and optically connected to the at least one optical input and the at least one optical output. In preferred embodiments, the instant integrated optical delivery devices comprise a plurality of optical outputs capable of optical coupling to a plurality of optical inputs on the target device.

Because the target waveguide devices of the instant analytical systems are designed to be removable, and because the tolerances between an optical delivery device and its associated target waveguide device must therefore be relatively relaxed, the optical output, or outputs, of the instant optical delivery device is configured to transmit an optical signal, or signals, through free space to a target waveguide device. In particular, the optical outputs of the delivery device are configured for optical coupling to the target device through free space at a distance of at least 1 mm, at least 2 mm, at least 3 mm, at least 5 mm, at least 10 mm, at least 20 mm, at least 30 mm, at least 50 mm, at least 100 mm, or even longer distances. In some embodiments, the device is configured for optical coupling to the target device through free space at a distance of at least 5 mm.

More specifically, the coupling can be at a distance of at least 10 mm. Even more specifically, the coupling can be at a distance of at least 20 mm.

The instant devices can be configured to deliver optical energy through free space in a variety of ways. In particular, the dimensions, shape, orientation, composition, and other properties of the optical components of the devices are chosen to provide such optical coupling through free space, as described in more detail below and in the Examples section. These and other features distinguish the instant devices and systems from similar devices and systems used for optical transmission and coupling in telecommunications and other related applications, where optical delivery devices, such as PLC devices, are coupled to their targets through extremely short distances. Indeed, the distances typically coupled in an integrated telecommunications optical device are on the order of 10 µm or even less. For example, U.S. Patent Application Publication No. 2014/0177995 discloses devices for optical coupling from an integrated device to an external optical fiber, where the outputs include couplers that comprise an integrated waveguide structure, a mirror structure, and a tapered vertical waveguide, where the vertical waveguide has apertures in the range of 0.1 to 10 µm and typical heights of 5-30 µm. These couplers, also known as vertical spot size converters, are designed for direct or nearly direct connection between the integrated waveguide structure and an associated output fiber. The devices optionally include a microlens of diameter less than 1 mm fabricated within the vertical waveguide. Another example of the direct, or nearly direct, coupling between an integrated waveguide device and an associated optical fiber is provided in U.S. Patent Application Publication No. 2015/0001175, which discloses the use of cylinder-shaped or sphere-shaped microlenses to facilitate optical coupling. The lenses are fabricated with radii roughly the same as the ~10 µm mode size of a typical telecommunications optical fiber, where the fiber is directly abutted with the microlens. These couplers are thus also designed for direct or nearly direct connection between the integrated waveguide structure and the output fiber at the time of device manufacture.

Figure 1A:
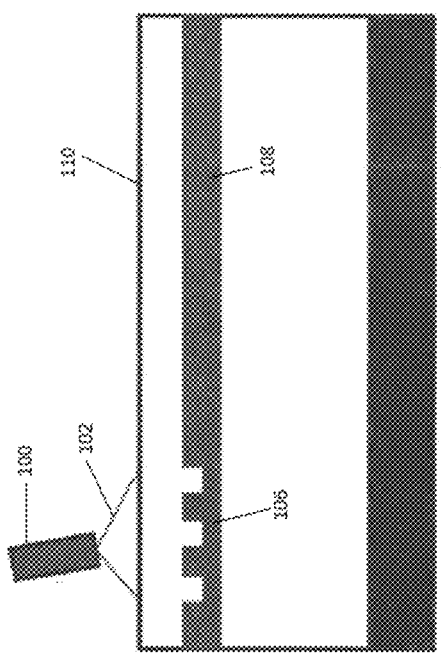
Figure 1C:
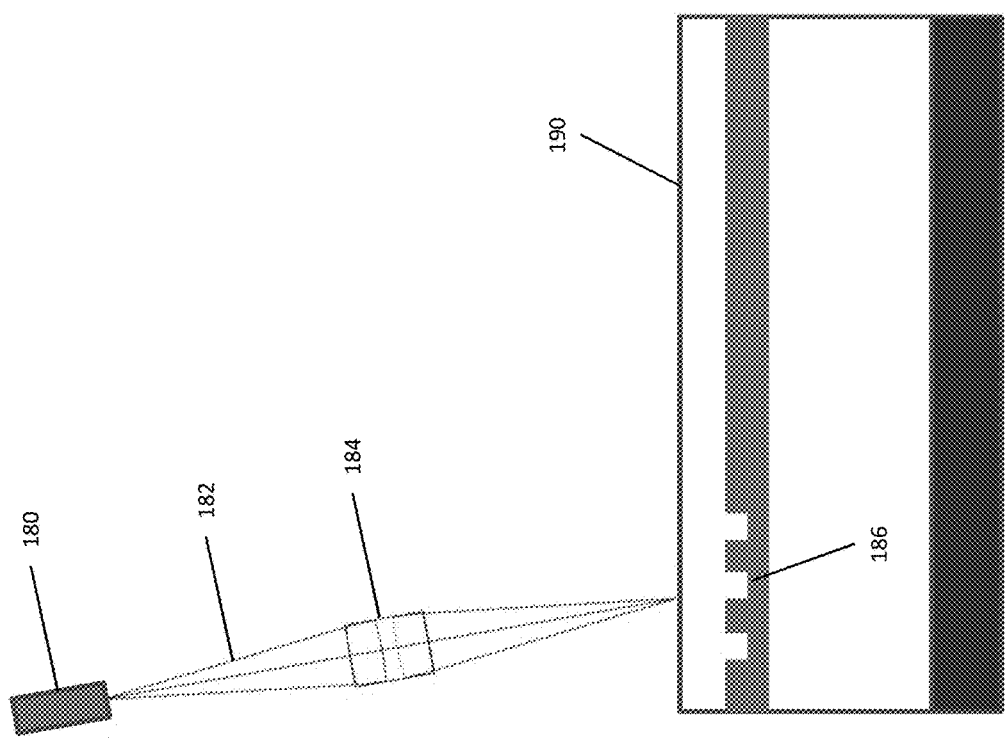

FIGS. 1A-1C provide a general comparison between optical delivery devices that are coupled directly, or nearly directly, to a target waveguide device and those, as disclosed herein, where coupling is through free space. As shown in FIG. 1A, where light is coupled from an optical fiber (100) to a target waveguide device (110), the optical beam (102) travels a relatively short distance to illuminate the target waveguide device with a footprint impinging on a grating coupler (106) that is optically connected to an integrated waveguide (108) in the target device. For comparison, as shown in FIG. 1B, the optical delivery devices of the instant disclosure (e.g., 150) emit an optical beam (e.g., 152) that travels a relatively longer distance to a target waveguide device (e.g., 160) and that illuminates a relatively larger footprint on the device. A correspondingly larger grating coupler (e.g., 156) and associated integrated waveguide (e.g., 158) are also shown in this drawing.

FIG. 1C illustrates an alternative embodiment of this type of optical system. Specifically, in this system, one or more optical elements (e.g., 184) are positioned between an optical delivery device (e.g., 180) and a target waveguide device (e.g., 190). Such optical elements can serve to focus, collimate, or otherwise modify an optical beam (e.g., 182) before it illuminates the target waveguide device. The optical element can, for example, modulate the focus of the beam to more closely match the numerical aperture (NA) of the grating coupler (e.g., 186) on the target device, as will be described in further detail below, and as would be understood by those of ordinary skill in the art. The optical element can likewise, for example, modulate the size of the footprint of the beam on the grating coupler, as desired. As should be understood from this example, the NA of the optical output of the optical delivery device need not exactly match the NA of the input coupler on the target device, since an intervening lens or other optical element can be used to modulate the optical properties of the beam between the optical delivery device and the target waveguide device.

Optical Coupling

The instant disclosure thus provides optical delivery devices with one or more optical outputs that are configured to couple light through free space to a target waveguide device. According to some embodiments, the numerical aperture (NA) of the optical outputs in the delivery devices can be modulated in order to facilitate and optimize coupling to the target device in various ways. As is understood by those of ordinary skill in the optical arts, NA is related to the range of angles within which light incident on a fiber or waveguide will be transmitted along the fiber or waveguide. It is a dimensionless value that is generally related to the refractive indices of the fiber or waveguide core and cladding. In the case of a step-index multi-mode optical fiber, numerical aperture can be calculated using the following equation:

$$NA = \sin\theta_{max} = \frac{1}{n}\sqrt{n_{core}^2 - n_{clad}^2}$$

where $\theta_{max}$ is the maximum acceptance angle of the fiber and corresponds to the half-angle of the fiber's acceptance cone—the cone of incident light capable of being propagated by the fiber, n is the index of refraction of the medium from which light enters or exits the core, $n_{core}$ is the refractive index of the core, and $n_{clad}$ is the refractive index of the cladding. The NA of a fiber or an integrated waveguide thus depends on the optical properties of the materials used to fabricate the core and the cladding of the fiber or waveguide and the size and geometry of the fiber or waveguide core. If the geometry of the core is chosen to be the single, lowest order, approximately Gaussian spatial mode, the NA can be further modified substantially, as the effective index of the core can be reduced owing to the mode power that extends into the cladding. Note that there are other more general geometries of the index distribution, such as variation in index of the core with radial or lateral position, and photonic bandgap constructions, which can also alter the NA or alter the distribution at a level of finer detail. The NA also depends on the wavelength of light being propagated through the core. It should thus be understood that the NA of a particular fiber or integrated waveguide can therefore be usefully modulated to obtain suitable behavior of the fiber or waveguide for a particular application and purpose.

From a practical standpoint, the NA of a given fiber or waveguide can also be determined empirically, for example by measuring the characteristics of propagated light emitted by the fiber or waveguide at a certain distance from the end of the device, for example using a direct far field scanner according to specification EIA/TIA-455-47. Such measurements provide empirical values of the mode field diameter (MFD), effective area, and numerical aperture of the fiber or waveguide. In the case of a single-mode fiber, the MFD is related to the spot size of the fundamental mode and represents a far-field power distribution of the optical output of the fiber. The relationship between NA and MFD is provided by the following equation, where λ is the wavelength of propagated light:

$$MFD = \frac{2}{\pi} \times \frac{\lambda}{NA}$$

Table 1 shows the relationship between NA and beam diameter for light of 532 nm, where the Gaussian beam profile is truncated at three different power levels: $1/e^2$, $1/e^3$, and $1/e^4$. The listed beam diameters at a power truncation of $1/e^2$ correspond to the MFD of the beam for each value of NA. The listed beam diameters at a power truncation of $1/e^3$ provide a useful estimation in designing the size of an optical coupler on a target device (i.e., the "footprint" on the target device). More specifically, a coupler of the cross-sectional size shown in this column will capture most of the energy from the transmitted beam.

Figure 1D:
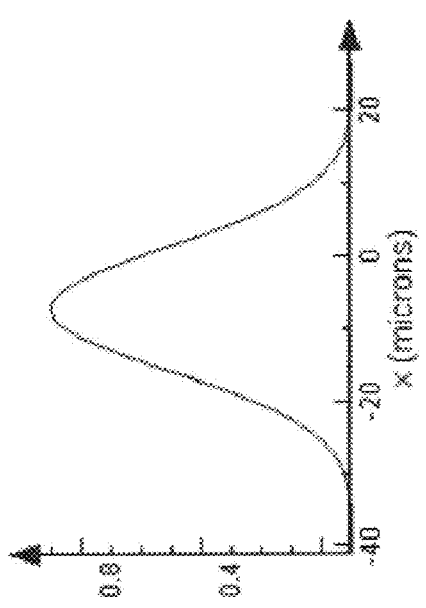
FIG. 1D shows a plot of the intensity of a Gaussian beam as a function of distance from the beam axis.

As is known in the art, NA values of 0.12 or higher are commonly used in devices for the transmission and coupling of optical telecommunications signals. As shown in Table 1, NAs of 0.12 and 0.13 result in relatively narrow beam diameters: 2.82 μm and 2.61 μm, respectively. By comparison, a Gaussian beam of 532 nm light with an NA of 0.01 displays a beam diameter of approximately 34 μm—over 10 times larger. FIG. 1D shows the 2-dimensional profile of such a Gaussian beam (NA equal to 0.01). As just noted, the beam diameter is determined by the truncation of beam profile at the $1/e^2$ power level.

TABLE 1

Power-truncated beam profiles for light of 532 nm as a function of NA.

| NA | $1/e^2$ (μm) | $1/e^3$ (μm) | $1/e^4$ (μm) |
|---|---|---|---|
| 0.13 | 2.61 | 3.91 | 5.21 |
| 0.12 | 2.82 | 4.23 | 5.64 |
| 0.05 | 6.77 | 10.16 | 13.55 |
| 0.015 | 22.58 | 33.87 | 45.16 |
| 0.01 | 33.87 | 50.80 | 67.74 |
| 0.005 | 67.74 | 101.60 | 135.47 |

It should also be understood that the diameter of a Gaussian beam will vary along the beam axis due to beam divergence. More specifically, for a divergent Gaussian beam propagated in free space, the beam radius, w, varies as a function of distance, z, along the length of the beam axis according to the equation:

$$w(z) = w_0 \sqrt{1 + \left(\frac{z}{z_R}\right)^2}$$

where $w_0$ is the minimum beam radius, i.e., the "waist radius", that occurs at a particular location along the beam axis known as the "beam waist", z is the distance from the beam waist along the beam axis, and $z_R$ is the Rayleigh length, a constant for a given beam that depends on the waist radius and the wavelength of light, λ, according to:

$$z_R = \frac{\pi w_0^2}{\lambda}$$

Accordingly, at a distance along the beam axis of $z_R$ from the beam waist, the beam radius is equal to $w_0\sqrt{2}$. In view of the above, it also follows that the Rayleigh length and the numerical aperture are related to one another according to the following equation:

$$NA = \frac{w_0}{z_R}$$

Figure 1E:
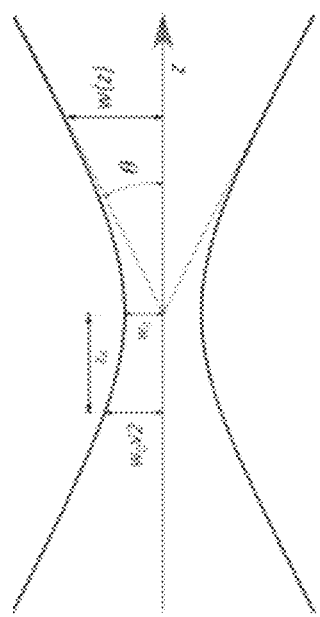
FIG. 1E illustrates the shape of a divergent Gaussian beam of radius w(z).

The above parameters are illustrated graphically in FIG. 1E, which represents a divergent Gaussian beam of radius w.

In accordance with the above description, fibers and waveguides with relatively larger NA values illuminate smaller footprints on a target surface and do so over a shorter distance through free space than those with relatively smaller NA values. These distinctions are apparent in the exemplary systems of FIG. 1A and FIG. 1B. Specifically, the optical fiber (100) of the system shown in FIG. 1A has a relatively high NA, and it therefore illuminates a relatively small footprint at a relatively close proximity to the target waveguide device (110). By comparison, the optical delivery device (150) of the system shown in FIG. 1B has a relatively low NA, and it therefore illuminates a relatively large footprint at a relatively large free-space coupling distance to the target device (160). As mentioned above, FIG. 1C shows an alternative design that permits the optical footprint of the output beam to be re-imaged with a target magnification, for example using an intervening optical element, to provide a beam waist of a preferred size at the surface of the target device. It should be noted here that the illustrations provided throughout the disclosure are not necessarily intended to represent accurately the dimensions, angles, or other specific design features of the devices illustrated, in particular any representation of divergence angles, waveguide bend radii, specific routing paths, and so forth.

As will be described in detail throughout the disclosure, the optical outputs of the disclosed delivery devices are designed to produce output beams that are readily and efficiently coupled through free space to their target devices. Free-space coupling, as disclosed in the devices and systems herein, provides several advantages relative to the direct coupling typically used in telecommunications and related systems. First, coupling through free space can avoid near-surface fiber tip to chip operation and is thus much easier for installation and operation and much less vulnerable to chip-surface dust and contamination and tip damage due to misoperation of integrated analytical systems with removable target waveguide devices. Second, as illustrated in FIG. 1B and FIG. 1C, coupling with low NA delivery devices through free space can allow larger beam footprint size on the target waveguide device, thus relieving thermal constraints on the target chip due to the injection of high laser power. Third, larger grating coupler size can also greatly alleviate optical source-to-chip spatial alignment difficulties. Fourth, free-space coupling can allow easier chip packaging solutions for the target chip, which, for example in a multiplexed DNA sequencing chip, needs to accommodate all the packaging interface requirements such as electrical, thermal, mechanical, and fluidics components. The output NA of the instant optical delivery devices can therefore be modulated in order to improve and optimize optical coupling to an associated target waveguide device.

Additional exemplary optical delivery devices illustrating modulation of device NA in the coupling of optical energy to a target waveguide device through free space are shown in FIGS. 2A-2C. For example, FIG. 2A illustrates a PLC (200) with an integrated waveguide (201), where the optical output from the waveguide is designed with a low NA (e.g., 0.01). The optical output thus produces a relatively narrow optical acceptance cone (202) that is configured to match the low NA of a target device and that can be effectively coupled to the target device through free space at a relatively large distance.

While it is generally desirable for the NA of the optical outputs in the instant delivery devices both to be relatively low and to match the NA of a target device, designing the integrated waveguides of a PLC to provide low NA output can under some conditions result in asymmetry or other losses as the light passes through free space from the PLC into the waveguide of the target device. As an alternative, the optical output of the PLC can itself be designed with a relatively higher NA than the target device (e.g., 0.05, 0.08, 0.09, 0.10, or even higher), for example as shown in the PLCs of FIG. 2B (220) or FIG. 2C (240), which each comprise an integrated waveguide (221 and 241, respectively). The resulting acceptance cones in these designs (222 and 242, respectively) are somewhat broader than the acceptance cone of device 200, and the resulting beam outputs can therefore be more naturally corrected using lenses either downstream from the PLC (for example, as shown in FIG. 2B for device 220 with lenses 224 and 226 in separate focusing element 228) or within the PLC itself (for example, as shown in FIG. 2C for device 240 with integrated lenses 244 and 246). Fabrication of PLCs with integrated waveguides having the relatively larger NAs of FIG. 2B and FIG. 2C can thus potentially lead to better chip performance. It should be understood in each of these embodiments that the NA of the delivery device's optical outputs are lower than the NA of the integrated waveguide itself, due to the presence of the lens element functionalities.

The NA of the instant optical delivery devices can thus be modulated in order to improve coupling to a target waveguide device through free space. In embodiments, the NA of the optical delivery device is modulated to match the NA of a target waveguide device. In some embodiments, the NA of the device is modulated to match the NA of a target waveguide device by optically coupling the delivery device to one or more lens elements. In more specific embodiments, the one or more lens elements are integrated into the optical delivery device.

According to some embodiments, the optical output of the instant devices has a numerical aperture of no more than 0.1, no more than 0.08, no more than 0.05, no more than 0.03, no more than 0.02, no more than 0.01, or even lower. In some embodiments, the numerical aperture is no more than 0.05. In specific embodiments, the numerical aperture is no more than 0.015.

As should be apparent from the comparison shown in FIG. 1A and FIG. 1B, although the NA of the traditional optical fiber (100) is significantly higher than that of the optical output of the instant optical delivery device (150), the surface area or "footprint" of the target device illuminated by light emitted from the instant optical device can be larger. As noted above, it can be advantageous to provide light with a larger optical footprint on the target device in order to minimize localized heating of the target device or to simplify alignment of the optical delivery device and the target device. In particular, the irradiance of the transmitted light is much lower than it would be if the light were transmitted in a more focused beam.

The exact footprint of light delivered to a target waveguide device will, of course, depend on the NA of the delivery device's optical outputs, the free space distance between the devices, and, for example as shown in FIG. 1C, the magnification of the free space optical system. In embodiments, the delivery device is configured to illuminate a footprint on the target waveguide device with a surface area per footprint of at least 144 $\mu m^2$, at least 225 $\mu m^2$, at least 400 $\mu m^2$, at least 625 $\mu m^2$, at least 900 $\mu m^2$, at least 1600 $\mu m^2$, at least 2500 $\mu m^2$, or even larger.

In other embodiments, the delivery device is configured to illuminate a footprint on the target waveguide device with a surface area per footprint of at most 250,000 $\mu m^2$, at most 62,500 $\mu m^2$, at most 22,500 $\mu m^2$, at most 10,000 $\mu m^2$, at most 6400 $\mu m^2$, at most 3600 $\mu m^2$, or at most 2500 $\mu m^2$.

In specific embodiments, the delivery device is configured to illuminate a footprint on the target waveguide device with a surface area per footprint of from 144 $\mu m^2$ to 250,000 $\mu m^2$, from 225 $\mu m^2$ to 62,500 $\mu m^2$, from 400 $\mu m^2$ to 22,500 $\mu m^2$, from 625 $\mu m^2$ to 10,000 $\mu m^2$, from 900 $\mu m^2$ to 6400 $\mu m^2$, or from 1600 $\mu m^2$ to 3600 $\mu m^2$.

In embodiments, the above-described illuminations are achieved at a free-space distance of from 1 mm to 100 mm. More specifically, the illumination can be achieved at a free-space distance of from 2 mm to 90 mm, from 5 mm to 80 mm, from 10 mm to 60 mm, or even from 20 mm to 50 mm.

It also follows from the above description that the instant optical delivery devices are capable of delivering relatively high levels of optical energy to a target waveguide device due to the relatively large footprints illuminated on the target device. Accordingly, in embodiments, the optical device is configured to illuminate a footprint on the target waveguide device with a power of at least 1 mW, at least 2 mW, at least 3 mW, at least 5 mW, at least 10 mW, at least 20 mW, at least 30 mW, at least 50 mW, at least 100 mW, or even higher per footprint. In specific embodiments, these power levels are achieved at a free-space distance of at least 10 mm.

According to another aspect of the disclosure, it can be desirable to modulate the design of the integrated waveguides in an optical delivery device in order to improve, for example, the coupling between an optical source and the optical inputs of the delivery device or, for example, the coupling between the optical outputs of the delivery device and a target waveguide device. In particular, it can be desirable to modulate the composition and shape of the integrated waveguides to achieve these effects. For example, it is known in the field of optics that mismatches between the mode sizes and effective indices between the highly confined mode of an integrated optical waveguide and the large diameter mode of an optical fiber input can result in coupling losses if not addressed. It can therefore be advantageous to taper the waveguide geometry or otherwise vary the waveguide structure and/or composition in order to improve the behavior and efficiency of the device, particularly in transitions between confined and unconfined optical modes. Such variation in structure and composition can include, for example, modulation of cladding composition and geometry or modulation of core composition and geometry, in particular modulation of core cross-sectional geometry. These and other features can be modeled and tested using widely available commercial software to predict and optimize the photonic properties of the devices prior to their fabrication.

Waveguide Splitting and Modulation of Optical Output

As just described, the numerical aperture and waveguide geometry and composition of the instant delivery devices can be modulated in order to improve the optical behavior and coupling efficiency of these devices with their targets. In addition, the devices can also include waveguide splitters, passive and active power modulation components, as well as other optical modulation components, to further refine the optical properties of the devices.

Figure 3:
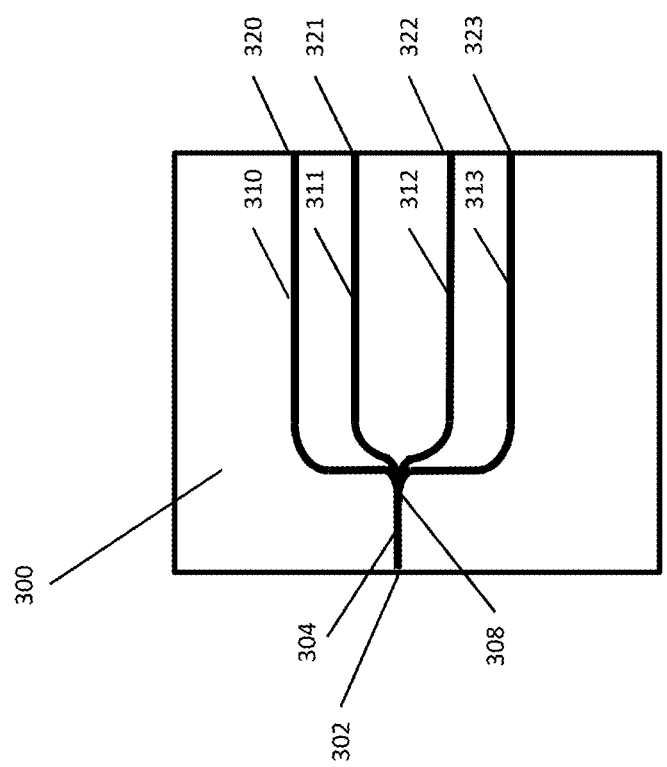
FIG. 3 illustrates an optical device layout, where a single optical input is split into four optical outputs with equal output intensities.

As already noted, PLC devices can include a variety of functional components embedded within the lightwave circuit. For example, a device can include an optical splitter, such that a single optical input can be divided into multiple optical outputs as optical energy is transmitted through the device. In the simplest case, for example as shown in the device of FIG. 3, the optical power emitted from each of the optical outputs of the device is the same, or nearly the same. In this example, the optical device (300) can include various integrated waveguides that are optically coupled with one another to transmit light through the device. Specifically, the device can include an optical input (302) optically coupled through an optical input waveguide (304) to a 1×4 splitting element (308) that divides the input optical energy delivered to four optical outputs (320-323) of equal power intensity that are optically coupled to the splitting element through four optical output waveguides (310-313). It should be understood that the same outcome could be achieved by a combination of a first 1×2 splitter followed by the further splitting of the resulting optical outputs by two additional 1×2 splitters.

Figure 4A:
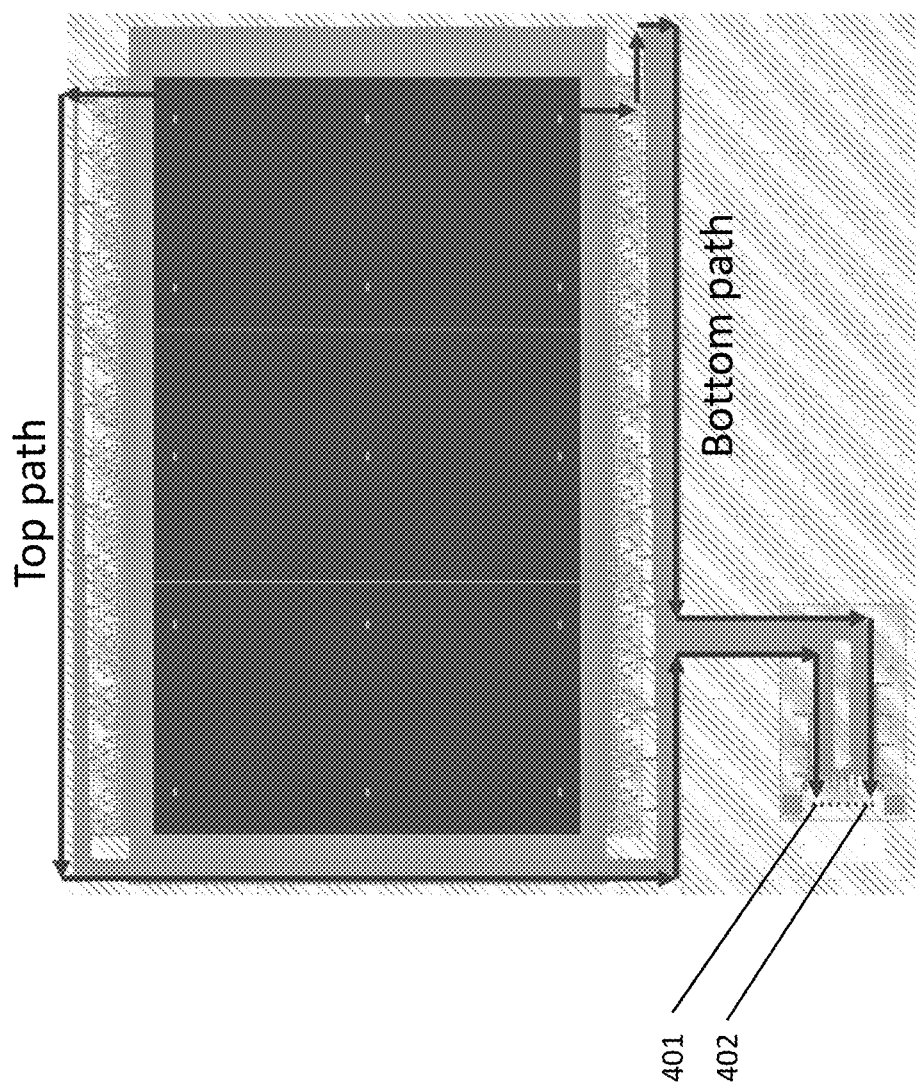
FIG. 4A and FIG. 4B show the layout of an exemplary target waveguide array and the relationship between block number and routing path length for two different optical paths on the array.
Figure 4B:
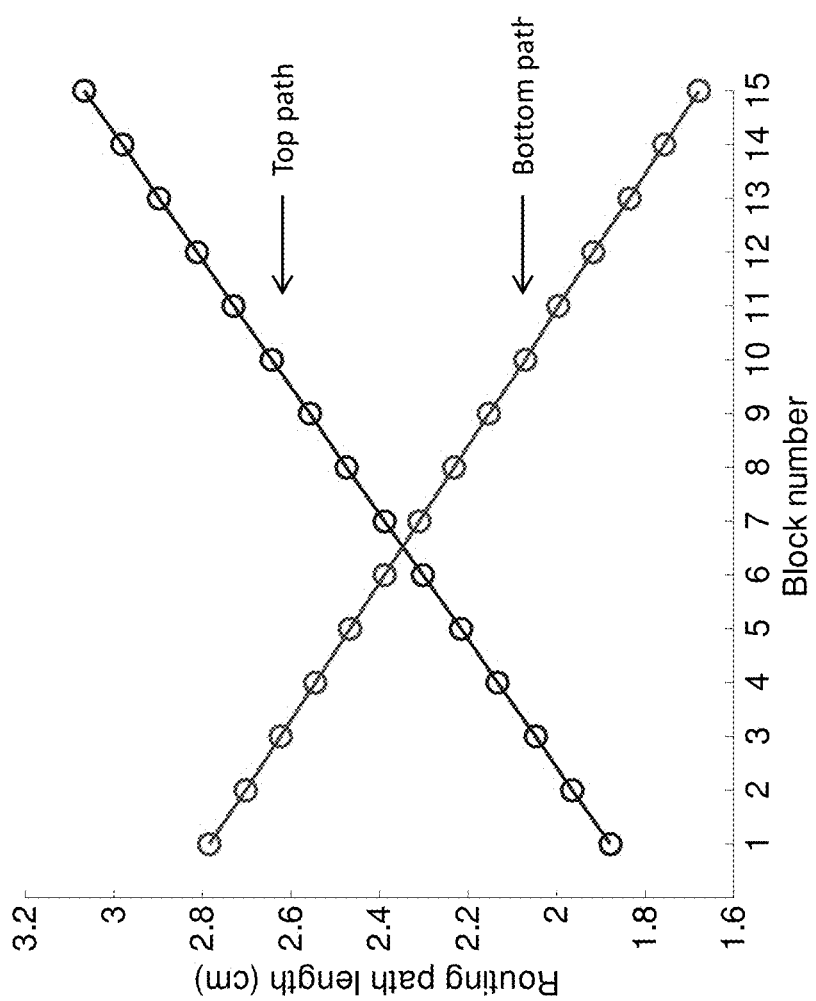

In some applications, it can be advantageous to vary the optical power emitted from each optical output of an optical delivery device according to the specific requirements of the target device. Accordingly, in some embodiments, the instant optical delivery devices are capable of balancing optical power levels according to the needs of the associated target waveguide device. For example, as illustrated in FIG. 4A and FIG. 4B, the routing loss for delivery of excitation light to the various locations on a target waveguide device can vary by location of the analyte on the device due to different routing path lengths. Specifically, FIG. 4A illustrates schematically the relevant paths on an exemplary target waveguide array. In this device, there are approximately 1,000,000 total nanowell sample sites, in an array of roughly 1000 rows by 1000 columns. Optical energy is delivered to the nanowells through a series of parallel integrated waveguides positioned below each column of nanowells. As shown for this array, light traversing the chip from a grating coupler at the bottom left corner of the chip to a waveguide located at the far right edge of the chip will travel significantly different path lengths depending on whether the light enters a grating coupler associated with the top path (e.g., grating coupler 401) or the bottom path (e.g., grating coupler 402). The use of a traditional PLC with equal power levels emitted from each output waveguide to deliver optical energy to such a chip would therefore result in variable power levels at the desired delivery locations within the subject waveguide for each optical signal, since the power level is directly dependent on the path length of the waveguide. Furthermore, as shown in FIG. 4B, the routing path length is directly related to the block number along the target chip (i.e., the left-to-right waveguide position along the chip).

Figure 5:
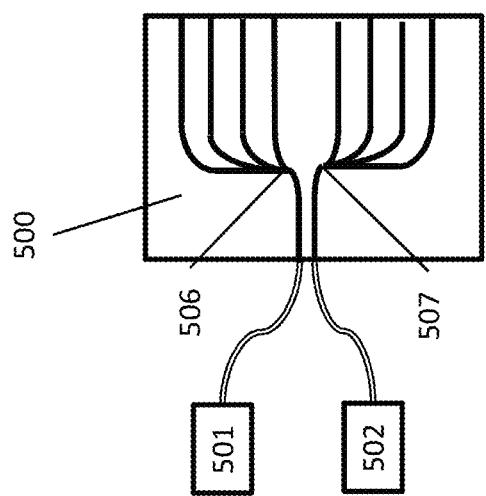
FIG. 5 illustrates an integrated optical device layout where the optical output of the device is matched to the target waveguide array. In this design, there are two optical inputs, and the optical outputs from the 1×4 splitter associated with each optical input are not equal.

Fundamental PLC technology provides for the splitting of input signals into any desired ratio of powers, however, so power equalization in the instant applications is no more difficult than that provided from an evenly balanced PLC. Such a PLC chip layout, where the optical output is matched to the target waveguide device, therefore has utility in the instant optical delivery devices. For example, in the layout illustrated in FIG. 5, PLC chip 500 receives input optical energy from two lasers (501 and 502), each of which is subject to a 1×4 splitter (506 and 507). This design is similar to the device of FIG. 3, except that splitters 506 and 507 deliver 10%, 18%, 27%, and 45% of the total laser input to the four optical outputs associated with each of the laser inputs, respectively, rather than 25%, 25%, 25%, and 25%. As noted above, these design features can be modeled and tested using widely available commercial software to predict and optimize the photonic properties of these components of the devices prior to their fabrication. Passive PLC splitters are well known and widely used in the telecommunications industry.

The modulation of power output from each output beam in the instant optical delivery devices can be achieved by any means, as would be understood by those of ordinary skill in the art. In some embodiments, rather than passively modulating optical output by an optical splitter, as described above, modulation is achieved actively using one or more variable optical attenuators (VOAs) fabricated within the optical delivery device. This approach allows the intensity of a given optical output to be modulated as desired as the device is being used, rather than having a fixed power output as defined by a splitter. VOAs are commonly used within a fiber optic communications line to reduce the optical fiber power to a certain desired level. Such VOAs can be, for example, fixed, step-wise variable, or continuously variable VOAs. VOAs can be used to reduce the power output of an optical beam within the instant optical delivery devices for example from 100% to 0.3%, or even lower, and to any specific output power within that range. In some embodiments, the attenuation range is from 1 dB to 20 dB.

Although VOAs in telecommunications applications are sometimes provided as an inline plug or patch cord, those used in the instant optical delivery devices are preferably integrated directly into the device itself. As a non-limiting example, an integrated optical Mach-Zehnder interferometer device can serve as the VOA in the instant optical delivery devices. See, e.g., U.S. Pat. No. 6,760,499, which describes the use of heat to modulate the differential birefringence of two inherently asymmetric waveguide arms and thus to attenuate an optical signal. Optical properties of integrated waveguides can usefully be altered by magnetostrictive, electrostrictive, or photostrictive induced stress, as is well known in the art. See, e.g., U.S. Pat. No. 5,502,781. An example of a Mach-Zehnder piezoelectric optical switch with low birefringence and a high extinction ratio is provided in PCT International Publication No. WO 00/52518.

The attenuation of optical power transmitted to a target integrated waveguide device, for example to one or more waveguides of a highly-multiplexed DNA sequencing chip, can be usefully controlled by feedback provided by the power-monitoring features described in more detail below. Specifically, output taps within the optical delivery device can be used to monitor the optical power being transmitted to the target waveguide. Alternatively, or in combination, measurement of optical power can be performed at a particular location within the target waveguide, for example at or near the nanowells of one of the highly-arrayed DNA sequencing devices described herein. Output levels measured at any of the just-described locations can be used in a feedback loop to modulate power provided by the optical delivery device and thus, in turn, to modulate optical power at the target locations.

In some delivery device embodiments, it can be useful to fabricate one or more other optical modulation components within the optical output waveguides of the device. For example, and as described in more detail below, one or more mode strippers can be included in the output waveguide. Alternatively, or in addition, one or more phase modulators or frequency modulators can be included in one or more output waveguides, in any combination.

Power Monitoring

The monitoring of optical power provided by an optical delivery device is also possible using standard chip fabrication technology, such as PLC technology, for example with PIN photodiodes or other detectors, either built into a PLC circuit monolithically, or attached, for example, in "flip-chip" fashion, as is known in the art. In some preferred embodiments, as disclosed herein, the actual application can be slightly different than usual. For example, if the optical delivery device is fabricated with a sufficiently thin top cladding, a PIN diode or other detector can be mounted on top of the device. Alternatively, or in addition, it can be desirable to exit a tap out of the side of the device and mount a PIN diode or other detector there. In some embodiments, a detector, detector array, or camera can be situated above the optical delivery device to quantify light power levels in the tap exit or in the guides directly. As used herein, a tap waveguide is a waveguide that extracts a small portion of an optical signal transmitted along a primary waveguide. The tap waveguide can therefore be used to monitor power levels in the primary waveguide.

Figure 6B:
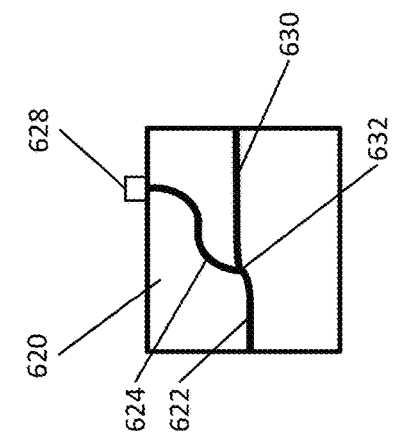
FIGS. 6A-6E illustrate configurations for power monitoring in various exemplary optical devices.
Figure 6D:
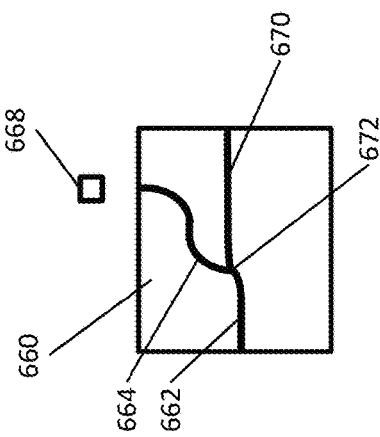
Figure 6A:
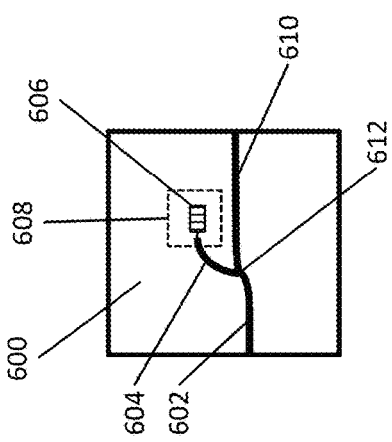
Figure 6C:
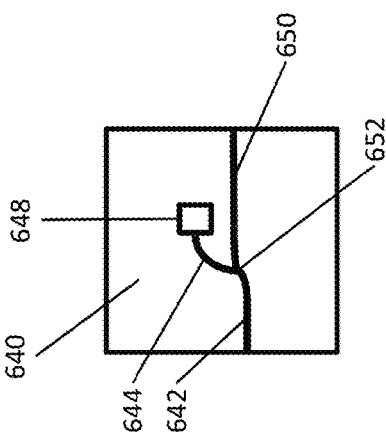
Figure 6E:
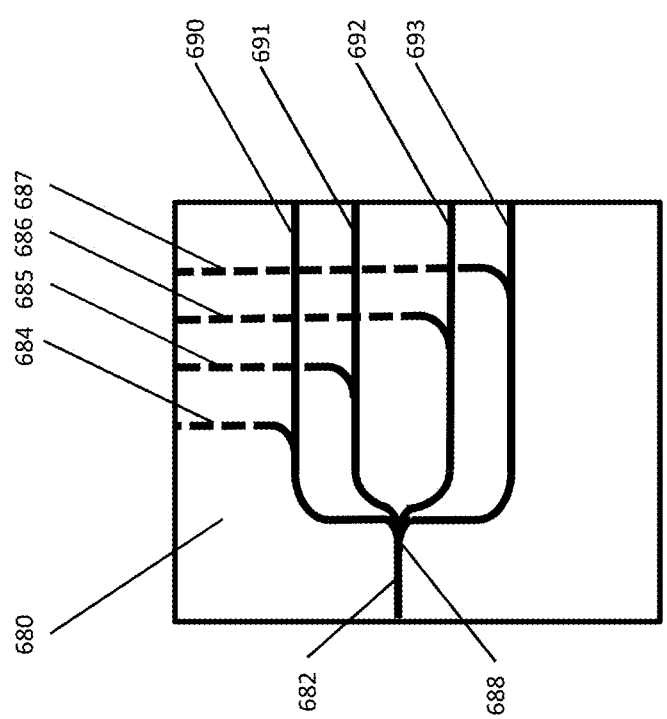

The above concepts are illustrated schematically in FIGS. 6A-6E. Specifically, these figures show 5 different optical delivery device embodiments (600, 620, 640, 660, and 680). In each case, the devices include an optical input waveguide (602, 622, 642, 662, and 682) and at least one output tap. In device 600, tap 604 is a 2% tap directed from splitter 612 to an output grating 606. An integrated detector positioned over dashed box 608 monitors the optical power transmitted through the tap as an indication of the power delivered to output waveguide 610. In device 620, tap 624 is a 2% tap directed from splitter 632 to a PIN detector 628 mounted on the side of the device. The PIN detector monitors the optical power transmitted through the tap as an indication of the power delivered to optical output waveguide 630. In device 640, tap 644 is a 2% tap directed from splitter 652 to a region of the PLC 648 with sufficiently thin cladding that a camera positioned over this space can monitor the optical power of the tap waveguide through free space. The measured power at region 648 is an indication of the power delivered to output waveguide 650. FIG. 6D shows a variant of the device of FIG. 6B, where in device 660, tap 664 is a 2% tap directed from splitter 672 to the side of the device. A camera, 668, positioned adjacent to the device monitors the optical power transmitted through free space from the tap as an indication of the optical power delivered to output waveguide 670. Device 680, shown in FIG. 6E, is a variant of device 660, where the input directed from splitter 688 to four output waveguides (690, 691, 692, and 693) is further diverted by four 2% tap waveguides (684, 685, 686, and 687) to the side of the device for measurement by one or more cameras adjacent to the side of the device for detection of optical signals through free space or by one or more PIN detectors mounted on the side of the device. As illustrated in this example, the tap waveguides can be designed to cross output waveguides 690, 691, 692, and 693 in the same plane without interfering with the output of optical energy from these waveguides.

Mode Stripping and Modulation of Polarization

In another aspect of the disclosure, light transmitted through the optical delivery devices of the instant systems can optionally be modified in various ways as it passes through the device. For example, as is well understood by those of ordinary skill in the art, input light sources used in some integrated waveguide devices can be highly sensitive to polarization extinction ratio (PER), and it can therefore be of use to mitigate PER effects in the instant optical delivery devices when used to deliver light to such target waveguides. In some embodiments, for example, "mode stripping" or "polarization cleanup" can be built into the waveguides of the optical delivery device. Such approaches can advantageously be less expensive than other possible approaches for addressing the sensitivity of the light sources to PER.

Figure 7A:
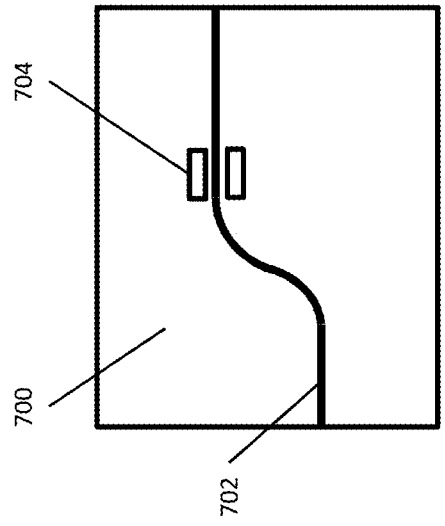
FIG. 7A and FIG. 7B illustrate the stripping of polarization from light transmitted through an optical delivery device, either by "mode" stripping (FIG. 7A) or by modulation of the bend radius or other waveguide features (FIG. 7B).
Figure 7B:
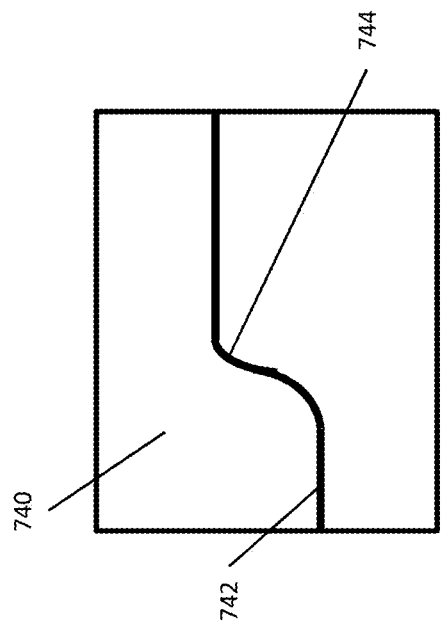

Two exemplary approaches for mitigating PER effects in an optical delivery device are illustrated schematically in FIG. 7A and FIG. 7B. In device 700, for example, as shown in FIG. 7A, an input optical waveguide 702 passes through a mode stripper 704, which preferentially removes optical inputs having undesirable polarization. Examples of attenuating unwanted polarization excitations in silicon on insulator (SOI) optical waveguide devices by integrating a TE- or TM-pass polarizer are known to those of ordinary skill in the art.

Alternatively, as illustrated in device 740, as shown in FIG. 7B, the input optical waveguide 742 is itself designed, for example in bend 744, to maximize loss of undesirable polarization. As is known to those of ordinary skill in the art, optical fibers, particularly single-mode optical fibers, can be designed to maintain or modulate polarization of light during its propagation through the fiber. For example, so-called polarization-maintaining (PM) fibers are capable of preserving polarization of light typically by introducing a systematic linear birefringence in the fiber, so that two well-defined polarization modes having distinct phase velocities are propagated along the fiber. Polarization maintenance can also be achieved by fabricating waveguides that are geometrically asymmetric, or that have a refractive index profile that is asymmetric, for example by utilizing an elliptical cladding, or by including rods or other substructures or features adjacent to the cores within the optical delivery device structure that are capable of producing stress birefringence. Alternatively, waveguides within an optical delivery device can be designed to generate circular birefringence, such as can occur by twisting a traditional single-mode fiber. The internal torsional stress thus created has a differential effect on the phase velocity of right-handed and left-handed polarized light propagated through the waveguide.

As just described, the above approaches are typically used to maintain the polarization of light transmitted through single-mode optical fibers, and these approaches can therefore be applied directly to the optical delivery devices in the instant systems where the input light has proper polarization. In situations where the input light has undesirable polarization, however, comparable approaches will be used to modulate the polarization of light passing through the waveguides of the optical delivery device and thus to provide improved optical inputs for target integrated waveguide devices, such as DNA sequencing arrays.

It can in some situations be advantageous to combine more than one feature in maintaining or modulating the polarization of light propagated through the waveguides of the instant optical delivery devices, for example by splitting, rotating, and/or recombining different polarization modes, for example as described by Zhang et al. (2010) Optics Express 18:25264 (dx.doi.org/10.1364/OE.18.025264).

Alternative Designs

Figure 8C:
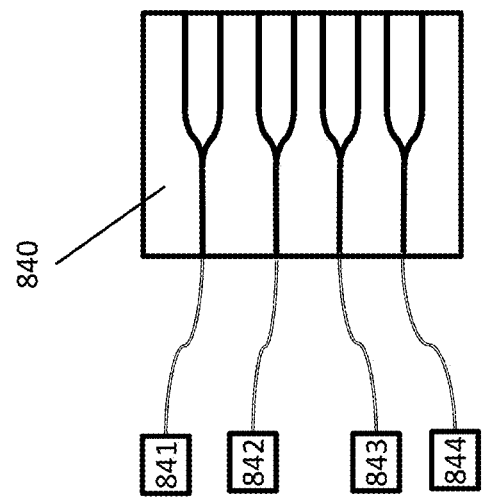
FIGS. 8A-8C illustrate three different optical delivery device embodiments capable of coupling optical energy into a multiplexed target waveguide array.
Figure 8B:
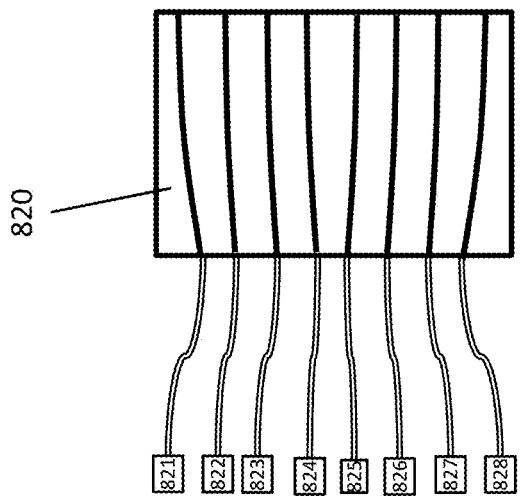
Figure 8A:
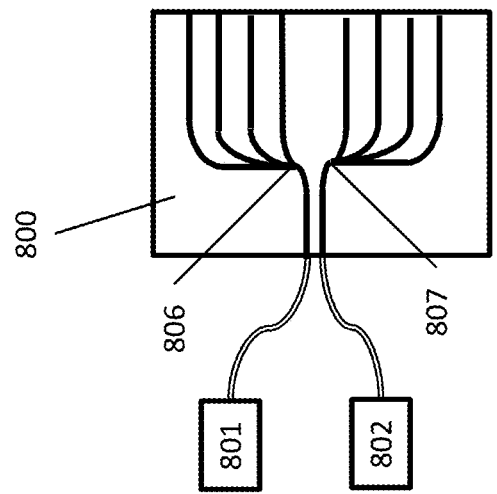

Three different optical delivery device embodiments (800, 820, and 840) that can be usefully associated with an optical analytical system are illustrated schematically in FIG. 8A, FIG. 8B, and FIG. 8C. In a simple embodiment, for example as shown in device 800, visible light from two lasers (801 and 802) is delivered to a PLC coupler chip by two optical fibers, where each fiber is directed into a 1×4 splitter (806 and 807) built into the device to provide 8 equally-spaced and equally-powered optical outputs. Input lasers are typically interfaced to the PLC using fiber pigtails or the like, and the optional inclusion of splitters within the PLC can simplify assembly of the systems and decrease their cost by limiting the number of fiber interconnections required.

Device 820 of FIG. 8B illustrates an alternative delivery device embodiment, where eight input optical signals (821-828) are directed into eight optical paths that traverse the device and result in eight equally-spaced and equally-powered optical outputs from a PLC coupler chip. A similar outcome can be achieved using input from four optical sources (841-844), as shown in device 840 of FIG. 8C, where each input is directed into a 1×2 splitter on a PLC chip to provide eight equally-spaced and equally-powered optical outputs.

Figure 9:
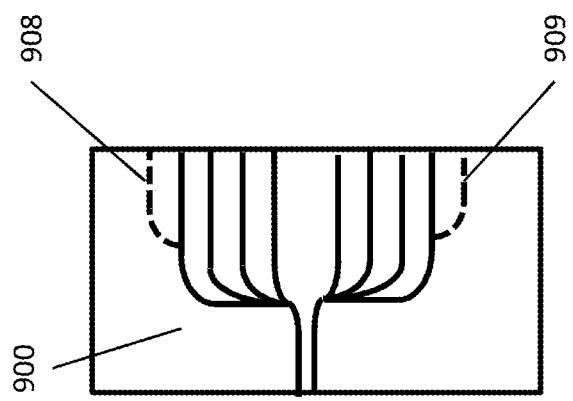
FIG. 9 illustrates an exemplary optical delivery device with two 2% output taps for use as alignment beams.

Device 900 of FIG. 9 illustrates yet another delivery device embodiment, where two optical input waveguides are each coupled to a 1×4 splitter, and the outermost output waveguides each include a 2% output tap (908 and 909) for use as alignment beams in coupling the optical output from the delivery device to a target waveguide device.

Further Advantages and Features of the Integrated Optical Delivery Devices

Use of a PLC in the optical delivery devices of the instant systems solves at least some of the problems that typically arise from use of separate components in an optical train. For example, there is a general problem that optical fibers have poor centration. Specifically, in the context of fiber optical systems, where the portion of the fiber carrying an optical signal (i.e., the "core") is significantly smaller than the surrounding "cladding", it is extremely difficult to align optical cores from device to device along an optical pathway, particularly when multiple adjacent optical cores within a device need to be properly aligned for optimal transmission efficiencies. A PLC, or similar optical delivery device, solves these problems by allowing precise transmission pathways to be designed and fabricated into the delivery device itself, thus minimizing the need for subsequent alignment of fiber cores during device assembly. This feature is particularly advantageous where multiple fibers need to be aligned or where such alignment needs to be maintained during the use of the device.

It should also be understood that the basic concepts described herein can be implemented in a variety of ways for a variety of purposes. For example, the principles used to design devices for delivery of optical energy to a target integrated waveguide device can also be used to collect optical energy from a device. For example, where the target waveguide device is an integrated DNA sequencing chip, similar principles can be used in designing optical collection devices to receive emission light from the nanowells of the sequencing chip. As mentioned above, optical fibers are widely used in the telecommunications industry both for delivering light to an optical device and for collecting light from the device. In the instant instruments, integrated optical devices, such as PLC couplers, could likewise both deliver excitation light into the waveguides of the associated DNA sequencing chip and collect emission light from the array of nanowells of the sequencing chip, for example to transmit the collected light to a detector, sensor, or other component on the detection side of the instrument.

In some embodiments, the instant optical delivery devices are configured for use with shorter wavelengths of optical energy than are typically used in the these devices. For example, telecommunications applications typically transmit light in the infrared range, most commonly at wavelengths of about 1310 nm or about 1550 nm. In some cases, lower cost electronics such as light-emitting diodes (LEDs) and vertical-cavity surface-emitting lasers (VCSELs), which typically operate at wavelengths of about 850 nm and 1300 nm, can be fabricated directly into an integrated optical delivery device. These devices are all designed to maximize transmission of optical energy over long distances by minimizing attenuation due to absorption and scattering, particularly at water band wavelengths.

In contrast to optical delivery devices used to transmit optical telecommunication signals, however, the instant optical delivery devices are designed for the efficient transmission of higher intensity optical energy for much shorter distances. In addition, the wavelengths of light transmitted by these devices are suitable for use with the optically active reagents commonly used in biological assays. These wavelengths are generally significantly shorter than those used for telecommunications purposes. In particular, the optical illumination used in DNA sequencing reactions with fluorescently-labeled DNA reagents, is typically in the visible range, most commonly in the range from 450 nm to 650 nm. The waveguides and other components of the optical delivery devices disclosed herein, and the associated target waveguide devices, for example the highly multiplexed analytical systems described above, are therefore preferably designed and scaled to transmit optical energy efficiently in the visible range. In some embodiments, the wavelengths range from about 400 nm to about 700 nm. In more specific embodiments, the wavelengths range from about 450 nm to 650 nm or even from about 500 nm to about 600 nm. In some specific embodiments, the wavelengths are from about 520 nm to about 540 nm, for example, approximately 532 nm. In other specific embodiments, the wavelengths are from about 620 nm to about 660 nm, for example, approximately 635 nm or 650 nm. In some embodiments, a combination of visible wavelengths can be transmitted within the devices.

In some uses, for example in systems involving the above-described integrated waveguides of a target device, such as a DNA sequencing device, it is highly desirable to deliver a pre-determined grid of laser spots that are aligned to an array of optical inputs associated with the integrated waveguides of the target device with high precision. For a traditional system, using multiple optical fiber inputs, this would require the mechanical alignment of each individual fiber entering the target device. Such mechanical alignment is typically not practical, however, due to the issue of centration. Alternatively, it is possible to use a particular optical delivery device, for example one of the integrated optical delivery devices described herein, to arrange the light sources with the degree of accuracy available from photolithographic fabrication techniques. The arranged light sources can be mapped onto an array of optical inputs, for example diffractive grating inputs or the like, within an associated target waveguide device, where those optical inputs can also be defined photolithographically. Absent the use of such an optical delivery device, alignment of the optical inputs would typically require a tedious and imprecise mechanical procedure involving a plurality of motors and a complex feedback system.

Integrated Optical Analytical Systems

Accordingly, in another aspect, the instant disclosure provides analytical systems comprising an integrated target waveguide device in combination with any of the optical delivery devices disclosed herein. As was already described, the instant optical delivery devices provide for the efficient coupling of optical energy to a target waveguide device through free space, for example at a distance of at least 1 mm, at least 2 mm, at least 3 mm, at least 5 mm, at least 10 mm, at least 20 mm, at least 30 mm, at least 50 mm, or at least 100 mm. As described above, the combination of these optical delivery devices with a target waveguide device provides an analytical system having various advantages over traditional coupled systems.

In some system embodiments, the optical output of the associated integrated optical delivery device has a numerical aperture of no more than 0.1, no more than 0.08, no more than 0.05, no more than 0.03, no more than 0.02, or no more than 0.01. In some embodiments, the optical delivery device is configured to illuminate a footprint on the target waveguide device with a surface area per footprint of at least 144 $\mu m^2$, at least 225 $\mu m^2$, at least 400 $\mu m^2$, at least 625 $\mu m^2$, at least 900 $\mu m^2$, at least 1600 $\mu m^2$, or at least 2500 $\mu m^2$. In other embodiments, the optical delivery device is configured to illuminate a footprint on the target waveguide device with a surface area per footprint of at most 250,000 $\mu m^2$, at most 62,500 $\mu m^2$, at most 22,500 $\mu m^2$, at most 10,000 $\mu m^2$, at most 6400 $\mu m^2$, at most 3600 $\mu m^2$, or at most 2500 $\mu m^2$. In still other embodiments, the device is configured to illuminate a footprint on the target waveguide device with a surface area per footprint of from 144 $\mu m^2$ to 250,000 $\mu m^2$, from 225 $\mu m^2$ to 62,500 $\mu m^2$, from 400 $\mu m^2$ to 22,500 $\mu m^2$, from 625 $\mu m^2$ to 10,000 $\mu m^2$, from 900 $\mu m^2$ to 6400 $\mu m^2$, or from 1600 $\mu m^2$ to 3600 $\mu m^2$.

In some system embodiments, the optical delivery device is configured to illuminate a footprint on the target waveguide device with a power of at least 1 mW, at least 2 mW, at least 3 mW, at least 5 mW, at least 10 mW, at least 20 mW, at least 30 mW, at least 50 mW, or at least 100 mW.

In some system embodiments, the system further comprises an intervening optical element between the integrated optical delivery device and the integrated target waveguide device. More specifically, the intervening optical element in these systems can be an optical lens element. In some system embodiments comprising an intervening optical element, the integrated optical delivery device comprises a plurality of optical outputs and at least one of the plurality of optical outputs has a numerical aperture of no more than 0.1, no more than 0.09, no more than 0.08, no more than 0.05, no more than 0.03, no more than 0.02, or no more than 0.01. In some embodiments comprising an intervening optical element, the integrated target waveguide device comprises a grating coupler optically coupled to an integrated waveguide, and the grating coupler has a numerical aperture lower than the numerical aperture of the optical output of the optical delivery device. More specifically in these embodiments, the grating coupler has a numerical aperture of no more than 0.05, no more than 0.03, no more than 0.02, or no more than 0.01. In specific system embodiments comprising an intervening optical element, the integrated optical delivery device comprises a plurality of optical outputs, and at least one of the plurality of optical outputs has a numerical aperture of no more than 0.1, no more than 0.09, no more than 0.08, no more than 0.05, no more than 0.03, no more than 0.02, or no more than 0.01, and the integrated target waveguide device comprises a grating coupler optically coupled to an integrated waveguide, and the grating coupler has a numerical aperture of no more than 0.05, no more than 0.03, no more than 0.02, or no more than 0.01.

In some system embodiments, the optical output waveguide of the optical delivery devices comprises a power modulator, such as a variable optical attenuator or even an integrated optical Mach-Zehnder interferometer.

In some system embodiments, the optical delivery device comprises one or more splitting elements optically coupled to the optical input of the device through an optical input waveguide. The splitting element or elements is optically coupled to a plurality of optical outputs through a plurality of optical output waveguides. In some embodiments, the splitting element or elements is optically coupled to a tap waveguide, and the optical delivery device can further comprise a power monitor optically coupled to the tap waveguide. In specific embodiments, the power monitor can control the power output transmitted by an optical output of the device. In specific embodiments, the power monitor can be an integrated detector or a camera. In some embodiments, the splitting element or elements is optically coupled to a tap waveguide, and the tap waveguide is optically coupled to an output grating or a region of thin cladding.

In some system embodiments, the optical delivery device comprises an amplitude modulator optically coupled to an optical output of the device through an optical output waveguide. The amplitude modulator can, in specific embodiments, be a variable optical attenuator.

In some system embodiments, the optical delivery device can comprise a mode stripper optically coupled to an optical output of the device through an optical output waveguide. In embodiments, the optical delivery device can be configured for optical output of visible light, for example visible light having a wavelength in the range from about 500 nm to about 600 nm.

In some system embodiments, the analytical system further comprises an alignment device. Such a component is particularly useful in systems where the target waveguide device is designed to be removable. In such a system, when a new target waveguide device is installed into the system, the alignment device can serve to adjust the position of the waveguide device relative to other components of the system, particularly with respect to the optical delivery device, and can thus optimize the coupling of optical energy from the optical delivery device to the target waveguide device. The alignment process can include a coarse alignment process, a fine alignment process, or both coarse and fine alignment processes. During the alignment process, the target waveguide device itself can be moved relative to the optical delivery device, the optical delivery device can be moved relative to the target waveguide device, or both devices can be moved relative to one another. In preferred system embodiments, the alignment device provides for the dynamic alignment of the integrated target waveguide device and the integrated optical delivery device, such that alignment between the components is maintained during the course of an analytical assay. In some system embodiments, the alignment device is a camera.

In some embodiments, the target waveguide devices of the instant analytical systems comprise an alignment feature. Such a feature can be used by an alignment device to effect alignment of the target waveguide device with other components of the system, such as, for example, the optical delivery device. In specific embodiments, the alignment feature can comprise a reference mark, for example a fiducial or other type of patterned region. The use of reference marks in the alignment of different components of an integrated system is well known in the art of printed circuit board manufacture and computer vision. See, for example, U.S. Pat. Nos. 5,140,646 and 7,831,098. In some specific embodiments, the alignment feature can comprise one or more waveguides. By monitoring the intensity of light transmitted through a waveguide tap or taps on the target waveguide device, and adjusting the alignment between the optical delivery device and the target waveguide device to maintain a desired intensity of light, alignment of the system during the course of an analytical assay can be maintained. In more specific embodiments, the alignment feature can comprise a plurality of low-power waveguide taps or a high-power beam tap.

In some embodiments, the analytical system further comprises an optical source, for example a laser or other such optical source. In other embodiments, the analytical system further comprises a plurality of optical sources, such as a plurality of lasers or the like. In specific embodiments, the optical source or the plurality of optical sources provides a modulated optical signal or a plurality of modulated optical signals. In more specific embodiments, the modulated optical signal or signals can be amplitude modulated, phase modulated, frequency modulated, or a combination of such modulations. Useful methods for improving the optical transmission of a waveguide by the modulation of input optical signals are described in U.S. patent application Ser. No. 15/003,589, filed on Jan. 21, 2016, the disclosure of which is incorporated by reference herein for all purposes.

The analytical systems of the instant disclosure can be used in a wide variety of different applications. Such applications can include the analysis of single molecules, and can involve observing, for example, single biomolecules in real time as they interact with one another. For ease of discussion, such multiplexed systems are discussed herein in terms of a preferred application: the analysis of nucleic acid sequence information, and particularly, in single-molecule nucleic acid sequence analysis. Although described in terms of a particular application, it should be appreciated that the devices and systems described herein are of broader application.

In the context of single-molecule nucleic acid sequencing analyses, a single immobilized nucleic acid synthesis complex, comprising a polymerase enzyme, a template nucleic acid whose sequence is being elucidated, and a primer sequence that is complementary to a portion of the template sequence, is observed in order to identify individual nucleotides as they are incorporated into the extended primer sequence. Incorporation is typically monitored by observing an optically detectable label on the nucleotide, prior to, during, or following its incorporation into the extended primer.

In order to obtain the volumes of sequence information that can be desired for the widespread application of genetic sequencing, e.g., in research and diagnostics, higher throughput systems are desired. By way of example, in order to enhance the sequencing throughput of the system, multiple complexes are typically monitored, where each complex sequences a separate DNA template. In the case of genomic sequencing or sequencing of other large DNA components, these templates typically comprise overlapping fragments of genomic DNA. By sequencing each fragment, a contiguous sequence can thus be assembled using the overlapping sequence data from the separate fragments.

A single template/DNA polymerase-primer complex of such a sequencing system can be provided, typically immobilized, within a nanoscale, optically-confined region on or near the surface of a transparent substrate, optical waveguide, or the like. These optically-confined regions are preferably fabricated as nanoscale reaction cells, also known as nanowells or zero mode waveguides (ZMWs), in large arrays on a suitable substrate in order to achieve the scale necessary for genomic or other large-scale DNA sequencing approaches. Such arrays preferably also include an associated excitation source, or sources, an associated emission detector, or detectors, and associated electronics. They thus comprise a fully integrated optical analytical system. Examples of analytical systems useful in single-molecule nucleic acid sequence analysis include those described in U.S. Pat. Nos. 6,917,726, 7,170,050, and 7,935,310; U.S. Patent Application Publication Nos. 2012/0014837, 2012/0019828, and 2012/0021525; and U.S. patent application Ser. No. 13/920,037; which are each incorporated by reference herein in their entireties.

Target waveguide arrays of integrated analytical devices, such as arrays of devices comprising nanowells, can be fabricated at ultra-high density, providing anywhere from 1000 nanowells per cm$^2$, to 10,000,000 nanowells per cm$^2$, or even higher density. Thus, at any given time, it can be desirable to analyze the reactions occurring in at least 100, 1000, 3000, 5000, 10,000, 20,000, 50,000, 100,000, 1 Million, 5 Million, 10 Million, or even more nanowells or other reaction regions within a single analytical system, and preferably on a single suitable substrate.

In order to achieve the ultra-high density of nanowells necessary for such arrays, the dimensions of each nanowell must be relatively small. For example, the length and width of each nanowell is typically in the range of from 50 nm to 600 nm, ideally in the range from 100 nm to 300 nm. It should be understood that smaller dimensions allow the use of smaller volumes of reagents and can, in some cases, help to minimize background signals from reagents outside the reaction zone and/or outside the illumination volume. Accordingly, in some embodiments, the depth of the nanowell can be in the range of 50 nm to 600 nm, more ideally in the range of 100 nm to 500 nm, or even more ideally in the range of 150 to 300 nm.

It should also be understood that the shape of the nanowell will be chosen according to the desired properties and methods of fabrication. For example, the shape of the nanowell can be circular, elliptical, square, rectangular, or any other desired shape. Furthermore, the walls of the nanowell can be fabricated to be vertical, or the walls of the nanowell can be fabricated to slope inward or outward if so desired. In the case of a circular nanowell, an inward or outward slope would result in, for example, a cone-shaped or inverted cone-shaped nanowell.

Using the foregoing systems, simultaneous targeted illumination of thousands, tens of thousands, hundreds of thousands, or even millions of nanowells in an array has been described. However, as the desire for multiplex increases, the density of nanowells on an array, and the ability to provide targeted illumination of such arrays, increases in difficulty, as issues of nanowell cross-talk (signals from neighboring nanowells contaminating each other as they exit the array), decreased signal:noise ratios and increased requirements for dissipation of thermal energy at higher levels of denser illumination, and the like, increase. The optical delivery devices of the instant specification address some of these issues by providing improved illumination of the target waveguide arrays to which they are coupled.

Target waveguide devices used in the instant analytical systems generally include a matrix, e.g., a silica-based matrix, such as silicon, glass, quartz or the like, polymeric matrix, ceramic matrix, or other solid organic or inorganic material conventionally employed in the fabrication of waveguide substrates, and one or more waveguides disposed upon or within the matrix, where the waveguides are configured to be optically coupled to an optical energy source such as the optical delivery devices described herein. Such integrated waveguides can be in various conformations, including but not limited to planar waveguides and channel waveguides. Some preferred embodiments of the waveguides comprise an array of two or more waveguides, e.g., discrete channel waveguides, and such waveguides are also referred to herein as waveguide arrays. Further, channel waveguides can have different cross-sectional dimensions and shapes, e.g., rectangular, circular, oval, lobed, and the like; and in certain embodiments, different conformations of waveguides, e.g., channel and/or planar, can be present in a single waveguide device.

In typical embodiments, a waveguide comprises an optical core and a waveguide cladding adjacent to the optical core, where the optical core has a refractive index sufficiently higher than the refractive index of the waveguide cladding to promote containment and propagation of optical energy through the core. In general, the waveguide cladding refers to a portion of the substrate that is adjacent to and partially, substantially, or completely surrounds the optical core. The waveguide cladding layer can extend throughout the matrix, or the matrix can comprise further "non-cladding" layers. A "substrate-enclosed" waveguide or region thereof is entirely surrounded by a non-cladding layer of matrix; a "surface-exposed" waveguide or region thereof has at least a portion of the waveguide cladding exposed on a surface of the substrate; and a "core-exposed" waveguide or region thereof has at least a portion of the core exposed on a surface of the substrate. Further, a waveguide array can comprise discrete waveguides in various conformations, including but not limited to, parallel, perpendicular, convergent, divergent, entirely separate, branched, end-joined, serpentine, and combinations thereof. In general, a waveguide that is "disposed on" a substrate in one of the instant devices, for example, an optical delivery device or a target waveguide device, can include any of the above configurations or combinations thereof.

A surface or surface region of a waveguide device is generally a portion of the device in contact with the space surrounding the device, and such space can be fluid-filled, e.g., an analytical reaction mixture containing various reaction components. In certain preferred embodiments, substrate surfaces are provided in apertures that descend into the substrate, and optionally into the waveguide cladding and/or the optical core. In certain preferred embodiments, such apertures are very small, e.g., having dimensions on the micrometer or nanometer scale.

It is an object of the integrated systems of the instant specification to couple optical illumination from an optical delivery device to a target waveguide device comprising an array of analytes (e.g., reaction components) of interest. Of particular interest is the ability to monitor single analytical reactions in real time during the course of the reaction, e.g., a single enzyme or enzyme complex catalyzing a reaction of interest. In embodiments, the waveguides of the subject target devices provide illumination via an evanescent field produced by the escape of optical energy from the optical core. The evanescent field is the optical energy field that decays exponentially as a function of distance from the waveguide surface when optical energy passes through the waveguide. As such, in order for an analyte of interest to be illuminated by the waveguide, it must be disposed near enough to the optical core to be exposed to the evanescent field. In preferred embodiments, such analytes are immobilized, directly or indirectly, on a surface of the target waveguide device. For example, immobilization can take place on a surface-exposed waveguide, or within an aperture in the device. In some preferred aspects, analyte regions are disposed in apertures that extend through the device to bring the analyte regions closer to the optical core. Such apertures can extend through a waveguide cladding surrounding the optical core, or can extend into the core of the waveguide.

Although primarily described herein in terms of channel waveguides, such apertures could also be constructed on a planar waveguide device, e.g., where the planar waveguide portion/layer is buried within the device, i.e., is not surface-exposed. Regions on the surface of a waveguide device that are used for illumination of analytes are generally termed "analyte regions", "reaction regions", or "reaction sites", and are preferably located on a surface of the device near enough to an optical core to be illuminated by an evanescent wave emanating from the optical core, e.g., on a surface-exposed waveguide or at the bottom of an aperture that extends into the device, e.g., into the waveguide cladding or core. The three-dimensional volume at a reaction site that is illuminated by the evanescent field of a waveguide core (e.g., to an extent capable of allowing detection of an analyte of interest) is generally termed the "observation volume" or "illumination volume". A region of a target waveguide device that comprises one or more analyte regions is generally referred to as a "detection region" of the device, and a single device can have one or multiple detection regions. Examples of such optical waveguides are provided in U.S. Pat. No. 7,820,983 and U.S. Patent Application Publication No. 2012/0085894, as described above.

As described above, and as illustrated in FIG. 4A and FIG. 4B, one of the limitations of waveguide illumination is optical attenuation as the light propagates down the waveguide, resulting in a reduction in power at different locations in the waveguide. For example, a particular laser intensity coupled into the waveguide will experience a slow decrease in energy density as light travels down the guide due to propagation losses, with the highest power at the end nearest the illumination source and the lowest at the end farthest from the illumination source. The degree of the propagation loss is typically a function of the designed geometry and manufacturing tolerances, and presents a challenge to performing multiplexed analytical reactions because it constrains the spatial range of the usable waveguide structure. It is important to maximize the distance over which the laser intensity is sufficiently uniform, in order to maximize the multiplex capabilities of the system. It is therefore an object of the present invention to provide uniform power over the length of a target waveguide device, e.g., to promote uniform illumination of all reaction sites to be illuminated by the waveguide.

In this context, it should be understood that light can be propagated from either direction within an integrated waveguide, and that propagation of light from each end of a waveguide simultaneously can in some circumstances help to mitigate propagation losses within the waveguide. In some circumstances it can be advantageous to propagate light from each end of a waveguide sequentially, rather than simultaneously, as would be understood by those of ordinary skill in the art. In other circumstances, and as described in more detail above, it can be advantageous to provide light of different intensities to different locations on a target waveguide or to modulate the intensity of light delivered to the target waveguide by the optical delivery device in order to mitigate propagation losses in the target waveguide. Other advantageous features and designs of target waveguides for use in the integrated analytical systems of the instant specification are disclosed in U.S. Patent Application Publication Nos. 2014/0199016 and 2014/0287964, which are incorporated by reference herein in their entireties.

Figure 13A:
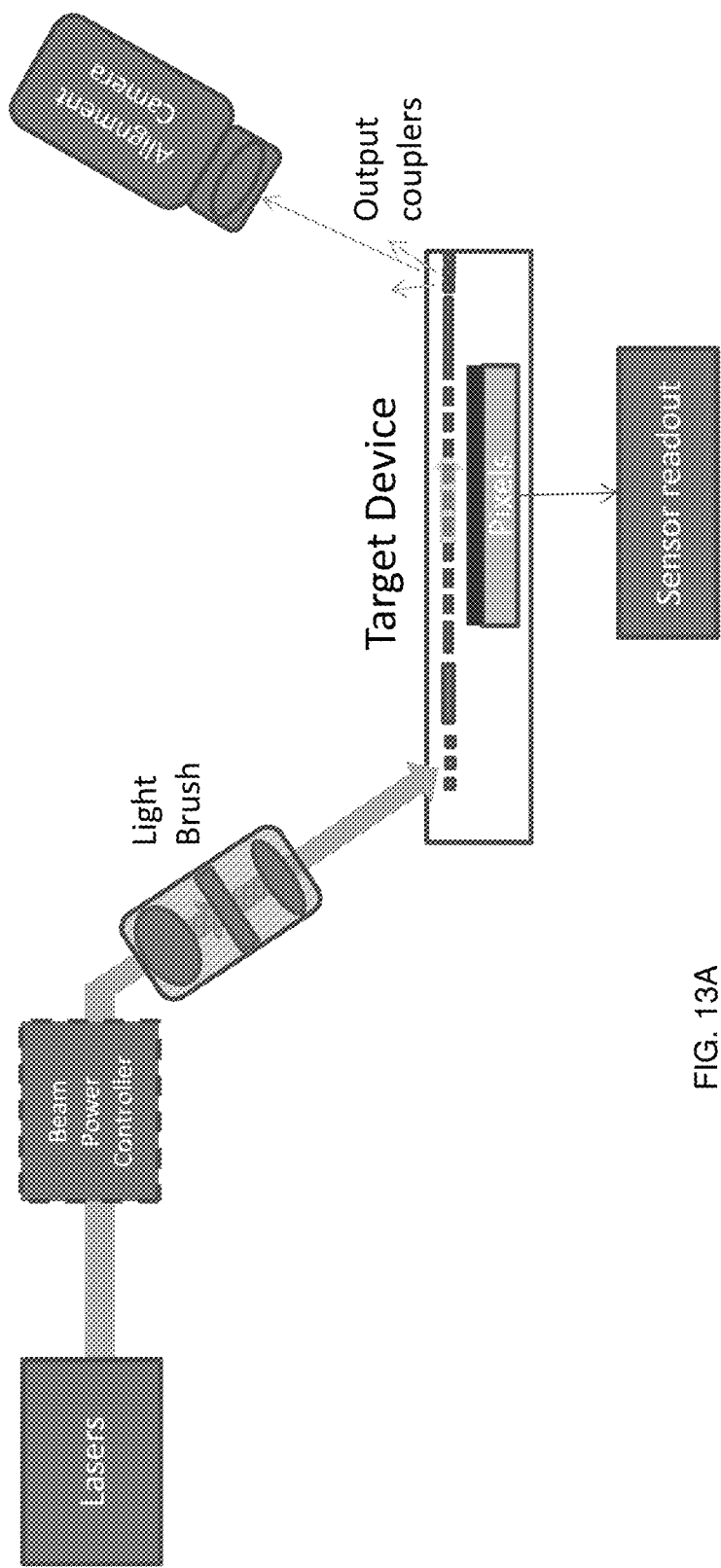
FIG. 13A shows an exemplary optical analytical system, including an optical source comprising lasers, a beam power controller, and a "light brush" planar light circuit to direct the optical output to the integrated target waveguide device. Also shown is an alignment camera.

FIG. 13A illustrates an exemplary optical analytical system of the instant disclosure, including a target waveguide device with at least one of the alignment features described herein. The system comprises an optical source consisting of one or more lasers, a beam power controller, and an optical delivery device (denoted as the "light brush"). The system also comprises an alignment camera, an integrated detector component comprising an array of "pixels" for detecting optical outputs from nanoscale sample wells arrayed across the target device, and a "sensor readout" component that receives and analyzes signals from the detector. An optical beam or beams emitted by the lasers and passing through the beam power controller and light brush is represented as a thick arrow that illuminates an input coupler on the target device. The optical input is coupled into the device and is directed to one or more integrated waveguides within the device, as indicated by the smaller arrow. The optical input can optionally be directed to one or more alignment waveguides and/or one or more power monitoring waveguides. The alignment camera in this drawing is shown receiving optical outputs indicated in the drawing by even smaller arrows, from output couplers at the far end of the device. These couplers could be used to output light from alignment waveguides and/or power monitoring waveguides. It should also be understood that the alignment camera can, in addition or alternatively, receive optical signals from other alignment features such as one or more patterned regions, fiducials, or other reference marks on the surface of the target device. Optical energy traveling through sample excitation waveguides illuminates samples in the arrayed nanowells, and fluorescence emitted from the samples is directed to appropriately aligned pixels in the detector layer, where the output signal is measured.

Figure 13B:
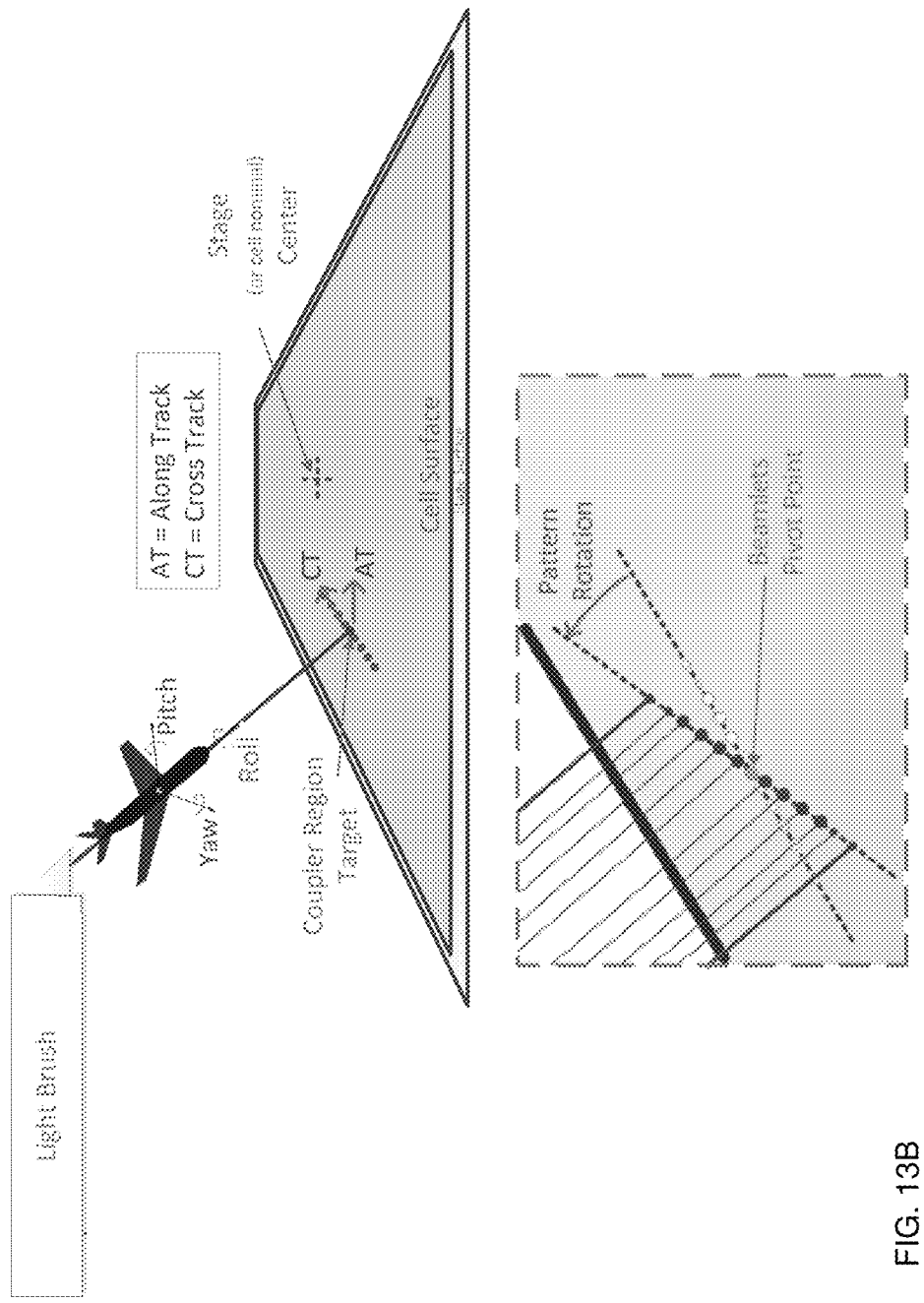
FIG. 13B shows the degrees of freedom to be controlled during the alignment of an optical delivery device and a target device. The motions are designated along track (AT), cross track (CT), pitch, yaw, and roll (or pattern rotation). Not shown is movement in the up-down dimension.

FIG. 13B illustrates in graphic form how the light brush of FIG. 13A can be aligned with a target waveguide device using any of the alignment features described above. Specifically, this figure illustrates the degrees of freedom that can be monitored and adjusted during the alignment of an optical source and a target device. As shown in the drawing, the airplane symbolizes three dimensions of rotation relative to the target device, and the "cell surface" corresponds to the surface of the target device. In addition to the rotational motions indicated in the drawing as pitch, yaw, and roll (or pattern rotation), the light brush and target device can move relative to one another in the x, y, and z coordinate space. Two of these motions are shown in the drawing as "along track" (AT) and "cross track" (CT) motions. Not shown in the drawing is an up and down motion to vary the distance between the light brush and target waveguide. As shown in the inset drawing, rotation on the "roll" axis causes the input beams to pivot around a particular axis. In this specific example, the light brush provides 12 separate input "beamlets". The two beamlets at each end of the illumination pattern are low-power alignment beamlets. Their targets on the device are illustrated as smaller circles in the line of input couplers on the surface of the device.

Modulation of Phase, Frequency, and Amplitude

In some embodiments, the optical delivery devices of the instant disclosure are designed to modulate the phase, frequency, and/or amplitude of optical signals transmitted by the devices. In some embodiments, the laser or other optical source in an analytical system is designed to provide modulated phase, frequency, and/or amplitude of optical signals transmitted by the devices. Transmission of such modulated optical signals can provide various benefits in the operation of the integrated analytical system and in the results obtained therefrom. See, e.g., U.S. patent application Ser. No. 15/003,589.

For example, in the case of an integrated multiplexed DNA sequencing system with a target waveguide device having the layout shown in FIG. 4A, the input optical energy can be delivered to each waveguide of the target device from both ends of the waveguide simultaneously. Such delivery allows for at least partial compensation of the routing losses resulting from different routing path lengths, as was described above, since a longer path length can be combined with a shorter path length within the same waveguide. This routing configuration can, however, result in an interaction between the two light beams within the waveguide in an artifact known as "speckle". In order to mitigate this artifact, the optical inputs can be provided at slightly different frequencies, for example, one input can provide excitation light at 530 nm, and the other can provide excitation light at 532 nm. Alternatively, or in addition, the phase of the light input into either end of the waveguide can be modulated to mitigate this artifact. Specifically, the phase of light coming out of the optical delivery device and destined for the two different paths can be modulated such that when the counter-propagating beams meet, they are in phase, and there is thus no interference. The phase and/or frequency of the two beams can be adjusted using feedback from the optical delivery device itself, for example by tuning the relative phases and/or frequencies to obtain the best signal, as would be understood by those of ordinary skill in the art.

In other embodiments, it can be desirable to modulate the amplitude of the optical signals transmitted to a target device. For example, and as was described in detail above, it can be desirable during an analytical measurement to monitor the optical power delivered to a target device in real time. Such power monitoring can, for example, provide feedback for adjusting and maintaining alignment between the optical delivery device and the target waveguide device, particularly where the optical energy is transmitted through free space between the devices. Where two optical beams are used to deliver light to one target waveguide device, however, it can be difficult to discern which beam is being measured in the power-monitoring analysis. For example, a small change in alignment can cause one beam to be more aligned and another beam to be less aligned, and it would be difficult to distinguish this difference absent the separate monitoring of output from both beams.

In the instant analytical systems, power monitoring of each optical beam entering a target device can be facilitated by placing a small amplitude modulation on top of the signal transmitted by the optical delivery device. For example, one signal can be modulated at frequency 1, and the other signal can be modulated at frequency 2, wherein the total amount of modulation is relatively small—e.g. approximately 1% of the total signal. In this system, if the intensity of one signal goes up and the intensity of the other signal goes down, it is readily apparent which signal is responsible for the change in power output.

Modulation of the optical signals transmitted by an optical delivery device can be achieved either by modulation of the laser or other optical source entering the device or can be achieved by modulation of the optical signal within the device itself, for example using variable optical attenuators fabricated directly into the device. Design and fabrication of such devices can be achieved by routine adaptation of the VOAs described above.

It is helpful to consider the modulation to be a "tag" for a given light beam exiting the optical delivery device. In the above-described embodiment, each signal is "tagged" with one modulation frequency. It should be considered within the scope of the invention, however, for each output beam from an optical delivery device to be tagged with a modulation frequency. Accordingly, a modulation tag can include more than two signals. For example, where there are multiple output beams, each output beam can be tagged with a different frequency.

Improved Alignment in V-Groove Fiber Arrays

Although pigtail connections and through-space coupling are preferably used to form the optical connections of the analytical devices and systems described herein, it can in some instances be advantageous to assemble multiple optical fibers directly into the optical inputs or outputs of a component of the instant analytical systems, in particular to maximize optical coupling and to maintain control of polarization of optical signals. In this regard, passively aligned V-groove arrays of fibers can be utilized to achieve this type of coupling, for example for coupling into a PLC or an arrayed waveguide device (AWD). Passively aligned V-groove arrays of fibers, however, assume no correlation among neighboring constituent fiber cores with respect to the cladding used to mechanically reference the cores. See, e.g., p. 8 of http://www.ozoptics.com/ALLNEW_PDF/DTS0083.pdf, which describes offset errors resulting from variations in the fiber core/cladding geometry of such assemblies. The choice of fiber preparation can in some cases result in concentricity errors being mirrored and thereby result in significant accuracy error (except for the trivial case of ideally concentric fibers). While some applications (e.g., telecommunications IR) have relatively large positional tolerances with respect to existing concentricity capabilities of fiber drawing, applications relying on the transmission of light in the visible spectrum suffer substantial insertion loss (IL) that can further differ from fiber to fiber when aligning a particular V-groove array to a matched array of waveguides (e.g., lithographically defined waveguides).

Figure 14C:
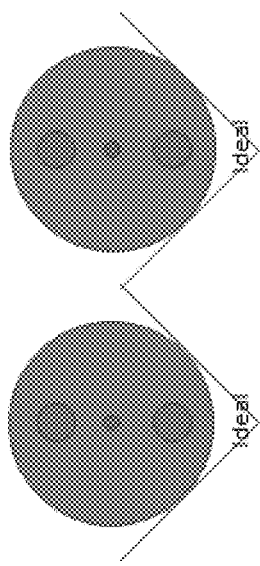
FIGS. 14A-14C illustrate the use of fibers having ideal concentricity error in a V-groove fiber array.
Figure 14A:
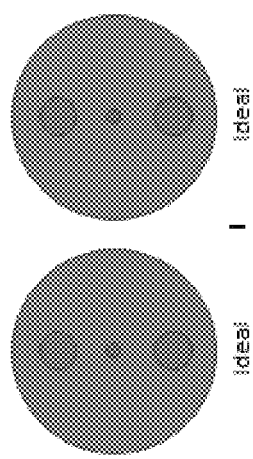
Figure 14B:
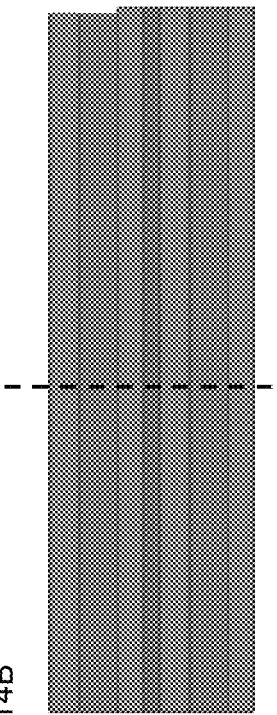

In order to overcome these difficulties, the fiber alignment methods disclosed herein exploit the axial correlation of core-to-cladding concentricity error to minimize deviation from accurate core-to-core spacing, in particular by using sequential lengths of fiber from a spool with a consistent choice of facet. In particular, it is desirable to ensure a fixed core-to-core distance (e.g., tolerance <<MFD~4 µm) despite uncertainty of ±0.5 µm in core-to-cladding concentricity error (applied to each fiber). For example, FIGS. 14A-14C show fibers with ideal concentricity that result in V-groove fiber arrays with ideal spacing. Specifically, FIG. 14A shows the mirrored end views of an ideal fiber cut as shown at the dotted line in the side view of FIG. 14B. FIG. 14C shows how an ideal fiber cut in this manner would be positioned within a V-groove array. As is apparent, alignment of such ideal fibers is not problematic. For comparison, however, FIG. 15 shows a V-groove array of fibers with lower tolerance (1 to ~4 µm=MFD) and flipped orientation within the array. As is apparent in this drawing, the center-to-center spacing in these V-groove fiber arrays is not conserved, and optimal alignment will be problematic. For comparison, however, if sequential segments of cut fibers are used in the arrays, as illustrated in FIG. 16A and FIG. 16B, a consistent core-to-core spacing can be maintained in the arrays. The consistent spacing assumes that the correlation length of the fiber is much less than the pigtail length, as would be understood by those of ordinary skill in the art. The dotted lines of FIG. 16B represent the longitudinal positions of the cross sections illustrated in FIG. 16A, and thus demonstrate the use of sequential lengths of fiber in the V-groove array.

This aspect of the disclosure therefore provides fiber arrays comprising a plurality of fiber segments, wherein each segment in the plurality of fiber segments is a sequential length of fiber from a single fiber segment and is assembled in the array with a consistent choice of facet. In some embodiments, the plurality of fiber segments are polarization maintaining fibers. In some embodiments, the plurality of fiber segments are configured to transmit visible light. In some embodiments, the fiber arrays are coupled to an integrated optical device, such as a PLC or an AWG.

It will be readily apparent to one of ordinary skill in the relevant arts that other suitable modifications and adaptations to the analytical devices and systems described herein can be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Example 1. Planar Lightwave Circuit with Tap Array at 532 nm

This example describes the design, optimization, and fabrication of a fibered chip, composed of a series of 11 single-mode waveguides to provide a PLC coupling function. An array of taps and photodiodes are also present on the PLC chip for laser-power-monitoring purposes. The modal behavior of the waveguide is optimized in the design process.

The PLC coupler prepared according to this example is an advanced optical component based on a combination of waveguides, taps, photodetectors, and polarization-maintaining fibers. The device is a passive waveguide chip that integrates eleven waveguides and concentrates the fiber cores into as small as possible an area. The process involves four main steps:

First, the waveguide process is optimized in order to create single-mode waveguides with a numerical aperture as close as possible to 0.072 and with a mode shape as round as possible.

Second, tap couplers are developed. Two types of taps are considered. In the first type, vertical taps extract a small portion of the light carried by the each waveguide and send it toward a photodetector for laser power monitoring. In the second type, two lateral taps extract a portion of the light carried by waveguides no 1 and no 11 of the PLC coupler, and send it through additional waveguides toward the end facet of the PLC coupler. The taps are designed, optimized, and precisely characterized in this process.

Third, the new PLC coupler chip is fabricated and packaged. Specifically, the chip design is based on the improved waveguide process of the first step and includes the two types of taps of the second step. A photodetector array is selected for purposes of monitoring the signals. A special package is designed to protect the PLC coupler chip and the fibers, as well as to integrate the photodetector array and its electrical connection into the device.

Fourth, cost and performance of the packaged device is evaluated.

Figure 10A:
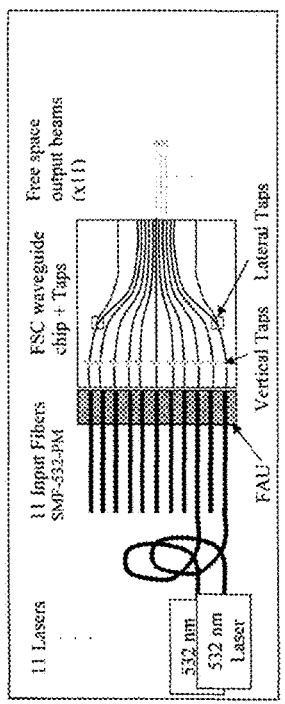
FIG. 10A illustrates an exemplary optical delivery device with 11 fiber inputs and both vertical and lateral taps.

A schematic representation of the above-described PLC coupler chip is provided in FIG. 10A. The chip is designed to be as small as possible compatible with fiber pigtailing and is designed to be compatible with a target photodetector array, for example an integrated DNA sequencing array. Specifications for the PLC coupler chip are outlined in Table 2, and additional details relating to each step are provided below.

TABLE 2

| Parameter | Value |
| --- | --- |
| Number of ports | 11 |
| Max chip size (L × W × H) | 20 × 10 × 3 mm³ |
| Wavelength range | 500-550 nm |
| Fiber to waveguide exit facet insertion loss | <2.2 dB* (<39% transmission loss) |
| Vertical TAPS extraction ratio | 0.1 to 2% |
| Lateral TAPS extraction ratio | 0.1 to 2% |
| Polarization extinction ratio (on any port) | >18 dB** |
| Back reflection for 0° angled facet | <−14 dB |
| Back reflection for 0° angled facet and AR coating | <−23 dB |
| Photodiode responsivity | >0.2 A/W |
| Output pitch | 10 μm |
| Crosstalk between ports | <−18 dB |
| Output waveguide N.A. | 0.072 |
| Input Fiber | PM460-HP |
| Fiber connector | FC/APC+ |
| Power handling | >300 mW |
| Operating temperature | 0° C. to + 50° C. |
| Storage | −20° C. to + 65° C. |

*For any polarization state
**For a PM fiber with at least an 18 dB PER

Step 1: Waveguide Process Optimization

An ion-exchange waveguide process is used and adapted in order to achieve waveguides with NA close to 0.072, while reducing the size of the PLC coupler and keeping the losses and crosstalk as low as possible.

a. NA Measurement Bench

An optical bench dedicated to the measurement of the waveguide numerical aperture is developed. The bench is based on the measurement of the far field profiles by a camera at various distances. The numerical aperture is determined at $1/e^2$ of the maximum profile intensity.

b. Development of a New Waveguide Fabrication Process

In some cases, it may be necessary to develop a new waveguide fabrication process in order to achieve the desired NA. Both process parameters and waveguide design are adjusted in order to bring the numerical apertures on the X and Y axes as close as possible to 0.072.

c. Determination of $R_{min}$ and Crosstalk

Based on the new waveguide manufacturing process, the minimum acceptable curvature radius is determined, as well as the optical crosstalk between adjacent waveguides, as a function of the waveguide parameters. This determination allows design optimization of subsequent PLC chips.

Step 2: Design and Optimization of Taps

Figure 10B:
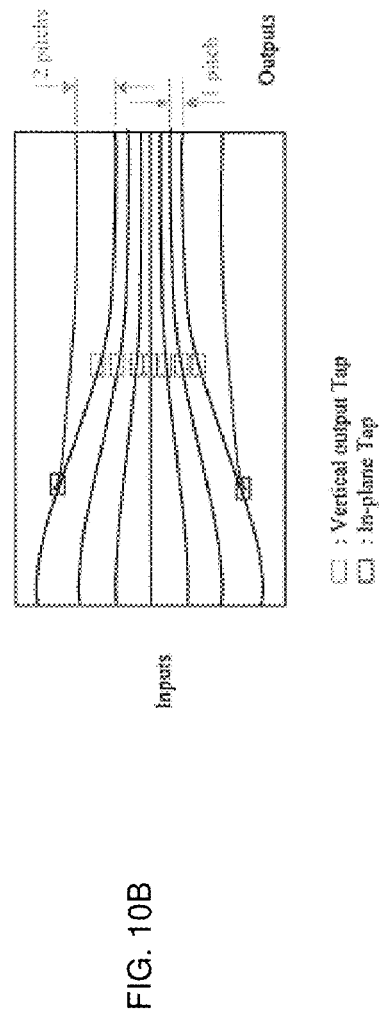
FIG. 10B shows the vertical and lateral taps in more detail.

Tap couplers that are compatible with the new waveguide-process from Step 1 are designed to optimize the coupling ratio of the chip and reduce losses. An exemplary PLC chip with Taps array is illustrated in FIG. 10B.

The new PLC chip typically contains both vertical and in-plane taps to monitor and manage optical power through the device. The goal is to reach a tap ratio in the 0.1-2% range while minimizing the additional optical loss. This ratio is determined with accuracy better than 10%. The in-plane taps are typically positioned on the first and the last channel of the device, as illustrated in FIG. 10A and FIG. 10B. The adapted design parameters are determined using a dedicated photolithography mask.

The vertical taps are typically prepared by depositing a diffracting object on top of the waveguide surface. Different geometries, sizes, and materials are tested to optimize the diffraction/loss ratio. One major point will also be the directivity of the diffracted light. Indeed, this light can be detected by a detector that may not be directly in contact with the glass surface.

An optical power budget is prepared by studying the vertical and in-plane taps, with the different sources of loss for each PLC chip. The tap ratio is accurately measured using a dedicated tool.

Step 3: Fabrication of PLC Coupler Prototypes

PLC Chip Design

The new PLC design includes an input coupling section, a fan-out section, 11 vertical taps, two lateral taps, and a numerical aperture (NA) adaptation section. The fan-out section is designed based on results of the bending loss study. A photolithographic mask is prepared based on different potential designs of PLC. The design is selected after fabrication and characterization of a series of wafers.

AR Coating of the Output Facet

After cutting and polishing of the PLC chip, the output facet is anti-reflective (AR) coated using standard processes.

Fiber Coupling

The chip is fibered with an eleven-port fiber array unit (FAU). The FAU is composed of eleven PM fibers (e.g., PM460-HP from Nufern). Each fiber is terminated with an FC:APC connector. The PM connectors are selected to be compatible with the small-core-fiber used, and to present low loss.

The loss of the fibered components is measured for each port. The result of the characterization is used as a base toward the definition of the final PLC specifications.

Photodetector Array Selection

In order to monitor the power of the lasers through the device, an array of tap couplers is added to the array of waveguides. The light extracted by the taps is sent toward an array of photodetectors. This photodetector array is selected so as to have the correct efficiency versus the amount of light extracted by the taps, and so that it is compatible in size with the PLC chip.

Packaging Design

The package is designed to protect the PLC chip and the fibers, to hold the photodetector array, and to hold the electrical connector. The PLC chip is precisely clamped onto the package. The un-sleeved fibers are protected by the package, and the sleeves are held by it. The photodetector array is placed above the PLC chip and is electrically connected to the instrument via an electrical connector installed on the side of the PLC chip package. The package has holes, so that it can be tightly screwed onto the instrument. Alternatively, or in addition, it will include a material compatible with magnetic holders.

Example 2. Planar Lightwave Circuit with Two Visible Wavelength Laser Inputs

Figure 11:
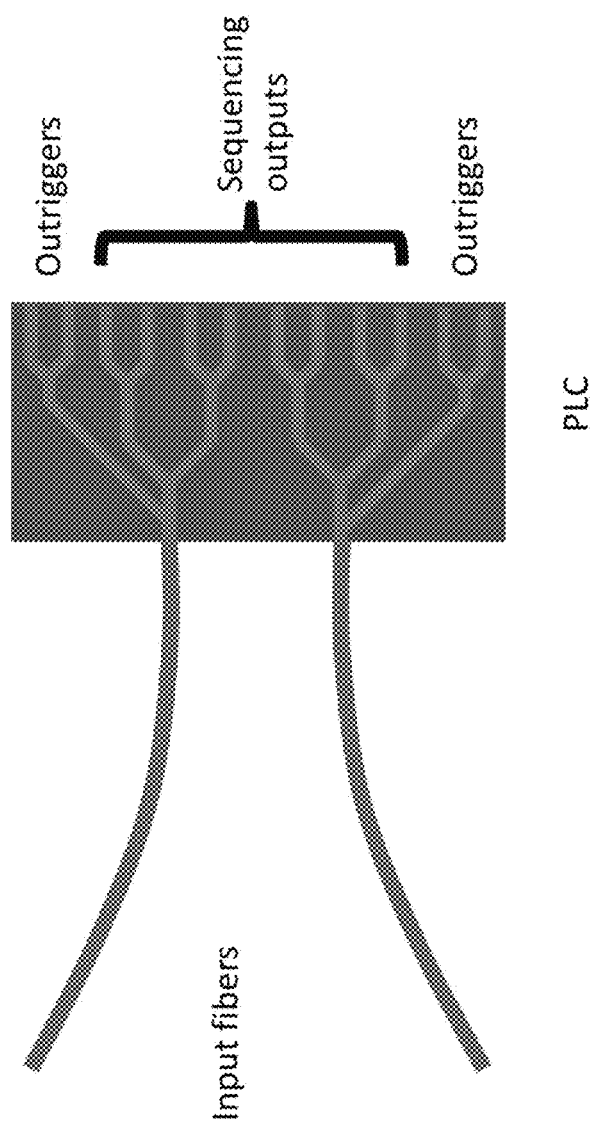
FIG. 11 illustrates an alternative exemplary optical delivery device with 2 optical inputs and a splitter that provides 8 outputs to sequencing waveguides and 4 "outriggers" for alignment of the optical delivery device to the target waveguide array.

This example provides an alternative PLC hardware coupler suitable for use in an integrated DNA sequencing system. The PLC coupler is designed to be included in a free space optical system. Specifically, the unit provides a source of structured illumination at 532 nm in a free space optical system for the sequencing product. The unit selectively splits and routes light from two input sources to eight main output sources, and two pairs of "outriggers" which are used for monitoring purposes. See FIG. 11.

Important features of the device include without limitation:
- Low insertion loss, and low back-reflection
- Maintenance of input PER
- Capable of high optical power
- Accurate symmetric and asymmetric power splits
- Accurate position of output waveguides
- Telecentric output
- Integration with high performance pigtails that are robust against typical handling, and a package that supports accurate placement in a larger opto-mechanical system The device comprises two input source fibers, each with a MFD corresponding to a beam far field NA of 0.072 ($1/e^2$), at a wavelength of 532 nm+/−2 nm, a PER of >20 dB, and a power of up to 300 mW. These fibers are then efficiently coupled (e.g., butt coupled) to two corresponding waveguides formed in the PLC. These waveguides are then each split into four main outputs of substantially similar power, and each also has two additional outrigger waveguides split with substantially lower power. These twelve total output waveguides then terminate on the output face, as illustrated in FIG. 12A and FIG. 12B.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. An analytical system comprising:
   an integrated optical delivery device; and
   an integrated target waveguide device;
   wherein the integrated optical delivery device comprises:
      a plurality of optical inputs;
      a plurality of optical outputs; and
      a plurality of optical output waveguides disposed on a substrate;
      wherein at least one optical output waveguide is optically connected to at least one optical input and at least one optical output;
      wherein at least one optical output is configured for optical coupling to the integrated target waveguide device through free space at a distance of at least 1 mm;
      wherein at least one optical output has a numerical aperture of no more than 0.1; and
      wherein the integrated target waveguide device is a multiplexed DNA sequencing device comprising at least 100 reaction regions.

2. The analytical system of claim 1, wherein the system further comprises an alignment device.

3. The analytical system of claim 1, wherein the integrated target waveguide device comprises an alignment feature.

4. The analytical system of claim 1, wherein the integrated target waveguide device comprises a grating coupler optically connected to an integrated waveguide.

5. The analytical system of claim 1, wherein the system comprises a plurality of optical sources.

6. The analytical system of claim 5, wherein the plurality of optical sources is a plurality of lasers.

7. The analytical system of claim 1, wherein the system further comprises a plurality of intervening optical elements between the integrated optical delivery device and the integrated target waveguide device.

8. The analytical system of claim 7, wherein the integrated target waveguide device comprises a grating coupler optically connected to an integrated waveguide, wherein the grating coupler has a numerical aperture lower than the numerical aperture of the optical output of the optical delivery device.

9. The analytical system of claim 1, wherein the integrated optical delivery device is configured to illuminate a footprint on the integrated target waveguide device with a surface area per footprint of at least 144 $\mu m^2$.

10. The analytical system of claim 1, wherein the integrated optical delivery device is configured to illuminate a footprint on the integrated target waveguide device with a surface area per footprint of at most 250,000 $\mu m^2$.

11. The analytical system of claim 1, wherein the integrated optical delivery device is configured to illuminate a footprint on the integrated target waveguide device with a surface area per footprint of from 144 $\mu m^2$ to 250,000 $\mu m^2$.

12. The analytical system of claim 11, wherein the integrated optical delivery device is configured to illuminate the footprint on the integrated target waveguide device at a distance of from 1 mm to 100 mm.

13. The analytical system of claim 1, wherein the integrated optical delivery device is configured to illuminate a footprint on the integrated target waveguide device with a power of at least 1 mW.

14. The analytical system of claim 13, wherein the integrated optical delivery device is configured to illuminate the footprint on the integrated target waveguide device at a distance of from 1 mm to 100 mm.

15. The analytical system of claim 1, wherein the integrated optical delivery device further comprises a splitting element optically connected to one optical input through an optical input waveguide and to a plurality of optical outputs through a plurality of optical output waveguides.

16. The analytical system of claim 15, wherein the integrated optical delivery device comprises at least four optical outputs and optical output waveguides.

17. The analytical system of claim 15, wherein the integrated optical delivery device comprises a plurality of splitting elements, each splitting element optically connected to one of a plurality of optical inputs through one of a plurality of optical input waveguides and to a plurality of optical outputs through a plurality of optical output waveguides.

18. The analytical system of claim 15, wherein at least one of the plurality of optical output waveguides is a tap waveguide.

19. The analytical system of claim 1, wherein the integrated optical delivery device delivers visible light to the integrated target waveguide device.

20. The analytical system of claim 19, wherein the visible light has a wavelength in the range from about 500 nm to about 600 nm.

21. An analytical system comprising:
   an integrated optical delivery device; and
   an integrated target waveguide device;
   wherein the integrated optical delivery device comprises:
      an optical input;
      a plurality of optical outputs; and
      a plurality of optical output waveguides disposed on a substrate;

wherein at least one optical output waveguide is optically connected to the optical input and at least one optical output;

wherein at least one optical output is configured for optical coupling to the integrated target waveguide device through free space at a distance of at least 1 mm;

wherein at least one optical output has a numerical aperture of no more than 0.1; and wherein the integrated target waveguide device is a multiplexed DNA sequencing device comprising at least 100 reaction regions.

22. The analytical system of claim 21, wherein the system further comprises an alignment device.

23. The analytical system of claim 21, wherein the integrated target waveguide device comprises an alignment feature.

24. The analytical system of claim 21, wherein the integrated target waveguide device comprises a grating coupler optically connected to an integrated waveguide.

25. The analytical system of claim 21, wherein the system further comprises an intervening optical element between the integrated optical delivery device and the integrated target waveguide device.

26. The analytical system of claim 21, wherein the integrated target waveguide device comprises a grating coupler optically connected to an integrated waveguide, wherein the grating coupler has a numerical aperture lower than the numerical aperture of the optical output of the optical delivery device.

27. The analytical system of claim 21, wherein the integrated optical delivery device is configured to illuminate a footprint on the integrated target waveguide device with a surface area per footprint of from 144 $\mu m^2$ to 250,000 $\mu m^2$.

28. The analytical system of claim 27, wherein the integrated optical delivery device is configured to illuminate the footprint on the integrated target waveguide device at a distance of from 1 mm to 100 mm.

29. The analytical system of claim 21, wherein the integrated optical delivery device is configured to illuminate a footprint on the integrated target waveguide device with a power of at least 1 mW.

30. The analytical system of claim 29, wherein the integrated optical delivery device is configured to illuminate the footprint on the integrated target waveguide device at a distance of from 1 mm to 100 mm.

31. The analytical system of claim 21, wherein the integrated optical delivery device further comprises a splitting element optically connected to the optical input through an optical input waveguide and to a plurality of optical outputs through a plurality of optical output waveguides.

32. The analytical system of claim 31, wherein the integrated optical delivery device comprises at least four optical outputs and optical output waveguides.

* * * * *